United States Patent
Destefano et al.

(10) Patent No.: US 11,672,905 B2
(45) Date of Patent: Jun. 13, 2023

(54) ROTATIONALLY BIASED INSERTION MECHANISM FOR A DRUG DELIVERY PUMP

(71) Applicant: AMGEN INC., Thousand Oaks, CA (US)

(72) Inventors: Mark A. Destefano, Collegeville, PA (US); Lawton Laurence, Phoenixville, PA (US); John C. Love, San Diego, CA (US); Ian B. Hanson, Wayne, PA (US); Paul F. Bente, IV, Wayne, PA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/951,893

(22) Filed: Nov. 18, 2020

(65) Prior Publication Data

US 2021/0069410 A1 Mar. 11, 2021

Related U.S. Application Data

(63) Continuation of application No. 16/819,443, filed on Mar. 16, 2020, which is a continuation of application
(Continued)

(51) Int. Cl.
*A61M 5/142* (2006.01)
*A61M 5/158* (2006.01)
*A61M 5/32* (2006.01)

(52) U.S. Cl.
CPC .... *A61M 5/14248* (2013.01); *A61M 5/14244* (2013.01); *A61M 5/158* (2013.01);
(Continued)

(58) Field of Classification Search
CPC .......... A61M 5/14248; A61M 5/14244; A61M 5/158; A61M 5/3287; A61M 2005/14252;
(Continued)

(56) References Cited

U.S. PATENT DOCUMENTS

| | | | |
|---|---|---|---|
| 5,104,380 A | * | 4/1992 | Holman ................. A61M 5/20 604/117 |
| 6,016,595 A | | 1/2000 | Dysarz |

(Continued)

FOREIGN PATENT DOCUMENTS

| | | |
|---|---|---|
| CN | 103764200 A | 4/2014 |
| CN | 203609736 U | 5/2014 |

(Continued)

OTHER PUBLICATIONS

International Search Report and Written Opinion, International Application No. PCT/US2016/017354, dated Oct. 5, 2016.
(Continued)

*Primary Examiner* — Kami A Bosworth
*Assistant Examiner* — Antarius S Daniel
(74) *Attorney, Agent, or Firm* — Marshall, Gerstein & Borun LLP

(57) ABSTRACT

An insertion mechanism for a drug pump includes an insertion mechanism housing; a sleeve; a rotational biasing member initially held in an energized state; a retraction biasing member and a hub connected to a proximal end of a needle, wherein the retraction biasing member is held initially in an energized state between the hub and the sleeve. The needle is inserted into a target tissue by the rotational biasing member and interaction between the hub and housing. Retraction of the needle is caused by decompressing or de-energizing of the retraction biasing member. A drug delivery pump includes an activation mechanism, a drive
(Continued)

mechanism, a sterile access connection, and the insertion mechanism. Assembly and operation methods are provided.

40 Claims, 26 Drawing Sheets

Related U.S. Application Data

No. 15/548,981, filed as application No. PCT/US2016/017354 on Feb. 10, 2016, now Pat. No. 10,625,018.

(60) Provisional application No. 62/147,403, filed on Apr. 14, 2015, provisional application No. 62/133,690, filed on Mar. 16, 2015, provisional application No. 62/114,200, filed on Feb. 10, 2015.

(52) U.S. Cl.
CPC .............. *A61M 5/3287* (2013.01); *A61M 2005/14252* (2013.01); *A61M 2005/1583* (2013.01); *A61M 2005/1585* (2013.01); *A61M 2205/13* (2013.01); *A61M 2205/18* (2013.01); *A61M 2205/44* (2013.01); *A61M 2205/581* (2013.01); *A61M 2205/583* (2013.01); *A61M 2207/00* (2013.01)

(58) Field of Classification Search
CPC .. A61M 2005/1583; A61M 2005/1585; A61M 2005/14256; A61M 2005/1426; A61M 5/20; A61M 2005/14284; A61M 5/46
See application file for complete search history.

(56) References Cited

U.S. PATENT DOCUMENTS

| | | | |
|---|---|---|---|
| 9,522,229 B2 | 12/2016 | Sonderegger et al. | |
| 10,918,788 B2 | 2/2021 | O'Connor et al. | |
| 2004/0064096 A1 | 4/2004 | Flaherty et al. | |
| 2008/0051714 A1 | 2/2008 | Moberg et al. | |
| 2008/0051730 A1 | 2/2008 | Bikovsky | |
| 2009/0099521 A1 | 4/2009 | Gravesen et al. | |
| 2011/0178461 A1* | 7/2011 | Chong | A61B 17/3415 604/151 |
| 2012/0209085 A1 | 8/2012 | Degen et al. | |
| 2013/0060233 A1* | 3/2013 | O'Connor | A61M 5/158 604/506 |
| 2014/0058353 A1* | 2/2014 | Politis | A61M 5/158 604/506 |
| 2014/0276413 A1 | 9/2014 | Baker et al. | |
| 2015/0164545 A1 | 6/2015 | Gyrn | |
| 2015/0297867 A1 | 10/2015 | Howell et al. | |
| 2015/0306307 A1* | 10/2015 | Cole | A61M 5/158 604/508 |
| 2017/0043133 A1* | 2/2017 | Amano | A61M 25/0631 |
| 2017/0296742 A1* | 10/2017 | Stefanov | A61M 5/14248 |
| 2018/0021508 A1 | 1/2018 | Destefano et al. | |

FOREIGN PATENT DOCUMENTS

| | | |
|---|---|---|
| WO | WO-02/092153 A2 | 11/2002 |
| WO | WO-2008/024810 A2 | 2/2008 |
| WO | WO-2008/133702 A1 | 11/2008 |
| WO | WO-2009/010399 A1 | 1/2009 |
| WO | WO-2009/013736 A1 | 1/2009 |
| WO | WO-2009/103736 A2 | 8/2009 |
| WO | WO-2012/108955 A2 | 8/2012 |
| WO | WO-2013/153041 A2 | 10/2013 |
| WO | WO-2014/011879 A2 | 1/2014 |

OTHER PUBLICATIONS

International Preliminary Report on Patentability, corresponding international application No. PCT/US2016/017354, dated Aug. 15, 2017.
European Patent Application No. 16710346.4, Communication Pursuant to Aritcle 94(3) EPC, dated Oct. 16, 2020.
Australian Patent Application No. 2020220074, Examination Report, dated Jul. 9, 2021.
Japanese Patent Application No. 2021-070810, Office Action, dated Feb. 15, 2022.
Chinese Patent Application No. 202011477312.3, Office Action, dated May 11, 2022.
Canadian Patent Application No. 2976047, Examination Report, dated Jun. 3, 2022.
European Patent Application No. 22201806.1, Extended European Search Report, dated Dec. 22, 2022.

* cited by examiner

ROTATIONALLY BIASED INSERTION MECHANISM FOR A DRUG DELIVERY PUMP

CROSS-REFERENCE TO RELATED APPLICATIONS

This is a continuation of U.S. patent application Ser. No. 16/819,443, filed Mar. 16, 2020, which is a continuation of U.S. patent application Ser. No. 15/548,981, filed Aug. 4, 2017, which is U.S. National Stage of PCT/US2016/017354, filed Feb. 10, 2016, which claims priority to U.S. Provisional Application No. 62/114,200, filed on Feb. 10, 2015, U.S. Provisional Application No. 62/133,690, filed on Mar. 16, 2015, and U.S. Provisional Application 62/147,403, filed on Apr. 14, 2015. The entirety of the foregoing is expressly incorporated herein by reference for all purposes.

FIELD

This invention relates to drug delivery pumps. More particularly, this invention relates to insertion mechanisms for drug delivery pumps, drug delivery pumps with safety integrated insertion mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections may imperfectly match the clinical needs of the patient, and can require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides insertion mechanisms for drug delivery pumps, drug delivery pumps with safety integrated insertion mechanisms, the methods of operating such devices, and the methods of assembling such devices. Additionally, the embodiments of the present invention provide sterile fluid pathways through the novel insertion mechanisms and drug pumps, which pathways are only engaged, connected, or opened upon proper activation by the user. Accordingly, the novel devices of the present invention alleviate one or more of the problems associated with prior art devices, such as those referred to above. The devices described herein may further include features which prevent the delivery of a medicament in too large a volume or at too rapid of a rate. By providing such automatic safety mechanisms, the safety of the patient may be ensured. Some medicaments, such as insulin, can be dangerous, and potentially even deadly, if they are not delivered according to prescribed parameters. The safety features described below may ensure that delivery of the medicament is terminated if delivery deviates from the specified parameters.

In a first embodiment, the present invention provides an insertion mechanism for a drug pump, said insertion mechanism including: an insertion mechanism housing having an internal chamber; a sleeve disposed within the housing; one or more rotational biasing members initially held in an energized state with at least a portion of the rotational biasing member engaged with the housing; a retraction biasing member; a hub connected to a proximal end of a needle, wherein the retraction biasing member is held initially in an energized state between the hub and the sleeve; and a fluid conduit which allows fluid flow from a drug container to the needle.

The insertion mechanism may further include a base connected to a distal end of the insertion mechanism housing. A sterile boot may be fixedly connected to the hub at a first end and secured between the sleeve and base at the other end. The term "sterile boot" is used to describe a boot within which certain internal components may reside, at one or more stages of operation, in a sterile condition. The boot need not be sterile through the entire operation of the mechanism or pump and, in fact, may not be initially sterile until assembly and sterilization of certain components has occurred. Additionally, the term "boot" is not intended to mean any specific shape or configuration, but is instead utilized to describe a component that can provide an interior space within which other components may reside at one or more stages of operation.

In another embodiment, the present invention provides a drug delivery pump with integrated safety features including a housing and an assembly platform, upon which an activation mechanism, a drive mechanism, a fluid pathway connection, a power and control system, and an insertion mechanism for a drug pump may be mounted, said insertion mechanism including: an insertion mechanism housing having an internal chamber; a sleeve disposed within the housing; one or more rotational biasing members initially held in an energized state with at least a portion of the rotational biasing member engaged with the housing; a retraction biasing member; a hub connected to a proximal end of a needle, wherein the retraction biasing member is held initially in an energized state between the hub and the sleeve; and a fluid conduit which allows fluid flow from a drug container to the needle.

The insertion mechanism may further include a base connected to a distal end of the insertion mechanism housing. A sterile boot may be fixedly connected to the hub at a first end and secured between the sleeve and base at the other end. In a further embodiment, the present invention provides a method of assembling the insertion mechanism including the steps of: connecting a hub to a proximal end of a needle; connecting a conduit to the hub; connecting a sterile boot to the hub; inserting the hub, needle, conduit, and sterile boot into the sleeve; placing a housing around the sleeve; and connecting a base to the sleeve by engagement of flex arms with apertures in the housing. The method may further include the step of inserting a retraction biasing member into the sleeve or housing of the needle insertion mechanism, in a position in which the retraction biasing member is constrained between the hub at one end and the sleeve or housing at the other end. A rotational biasing member may be placed around the housing such that a portion of the rotational biasing member is engaged with a portion of the housing, thereby coupling de-energizing of the biasing member with rotation of the housing.

In yet another embodiment, the present invention provides a method of operating the drug delivery pump. The method of operation includes: triggering an activation mechanism to disengage a rotation prevention feature from an insertion mechanism housing, wherein such disengagement permits a rotational biasing member to de-energize and cause a rotation of the housing, wherein such rotation causes distal translation of a hub and needle disposed within the housing which drives insertion of the needle and/or flexible cannula into the body of a user; connecting a fluid pathway connection having a piercing member to a drug container having a pierceable seal; and activating a drive mechanism to force a fluid through the fluid pathway connection, the conduit and the needle, and into the body of a user. The method further includes causing and/or allowing further de-energizing of the rotational biasing member thereby causing further rotation of the housing. This rotation allows a retraction biasing member to expand and cause proximal displacement of the hub and needle, thereby retracting the needle from the target tissue. In such an embodiment, a flexible cannula may remain in the target tissue, after needle retraction, such that delivery may continue. In a preferred embodiment, the method of operation may further include: first displacing one or more on-body sensors to permit displacement of the activation mechanism.

According to a feature of the disclosure, there is provided an insertion mechanism for a drug pump. The insertion mechanism has an axis (A) and includes a rotatably disposed housing, at least one rotational biasing member, a sleeve, a needle, a hub, and at least one retraction biasing member. The at least one rotational biasing member is coupled to the housing and initially held in an energized state. The rotational biasing member is disposed to rotate the housing as the rotational biasing member de-energizes. The sleeve, needle, and hub are disposed at least partially within an internal chamber of the housing. The needle has a hollow interior, a proximal end, and a distal end. The hub is connected to the proximal end of the needle. The needle and hub are configured to axially translate between an initial position and an insertion position. The at least one retraction biasing member is disposed between the hub and at least one axially-stationary element. The retraction biasing member is disposed to move the hub and needle from the insertion position to an at least partially retracted position as the retraction biasing member de-energizes. Rotation of the housing caused by de-energizing of the rotational biasing member causes axial translation of the hub and needle in a distal direction from the initial position to the insertion position and de-energizing of the retraction biasing member causes translation of the hub and needle in a proximal direction to the at least partially retracted position.

According to another feature of the disclosure, there is provided such an insertion mechanism including a cannula having a lumen. The cannula is disposed at least partially within the internal chamber of the housing and a distal end of the needle is disposed at least partially within the lumen of the cannula. Initial rotation of the housing caused by de-energizing of the rotational biasing member causes axial translation of the hub, the needle, and the cannula in a distal direction from the initial position to the insertion position. Further secondary rotation of the housing caused by de-energizing of the rotational biasing member allows de-energizing of the retraction biasing member, which causes translation of the hub and needle in a proximal direction to the at least partially retracted position wherein the needle is disposed at least partially inside of the lumen of the cannula.

According to yet another feature of the disclosure, there is provided such an insertion mechanism wherein the at least one retraction biasing member is disposed to further move the hub to a fully retracted position wherein the needle is no longer disposed within the lumen of the cannula. In this embodiment, further, tertiary rotation of the housing caused by de-energizing of the rotational biasing member allows de-energizing of the retraction biasing member, which causes translation of the hub and needle in a proximal direction to the fully retracted position to terminate flow of medicament through the cannula. The tertiary rotation is initiated by a termination mechanism.

According to a further feature of the disclosure, there is provided a drug pump including a drug pump housing, an activation mechanism, a drive mechanism, and an insertion mechanism having an axis (A). The insertion mechanism includes a housing having an internal chamber, at least one axially-stationary element, a needle, a hub, and at least one retraction biasing member. The at least one axially-stationary element includes a sleeve. The sleeve, the needle, and the hub are at least partially within an internal chamber of the housing. The needle has a hollow interior, a proximal end, and a distal end. The hub is connected to the proximal end of the needle. The needle and hub are configured to axially translate between an initial position, an insertion position, and a retracted position wherein the distal end of the needle is disposed within at least one of the housing and the at least one axially-stationary element. The at least one retraction biasing member is disposed between the hub and at least one axially-stationary element. The retraction biasing member is disposed to move the hub and needle from the insertion position to a retracted position as the retraction biasing member de-energizes. The retraction biasing member is permitted to de-energize to retract the hub and needle to the retracted position in response to a termination mechanism including at least one of a user input, a device operation error, and an end-of-dosage signal.

According to yet another feature of the disclosure, there is provided a method of operating a drug pump including one or more of the disclosed insertion mechanisms. The method includes permitting the at least one rotational biasing member to de-energize from its initial energized state, wherein such de-energizing causes rotation of the needle housing and thereby causes translation of the needle and hub in the distal direction from the initial position to the insertion position; connecting a sterile access connection to a drug container; and activating a drive mechanism to force a fluid through the sterile access connection, the conduit, the needle, and into the target.

Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein.

DETAILED DESCRIPTION

Figure 1A:
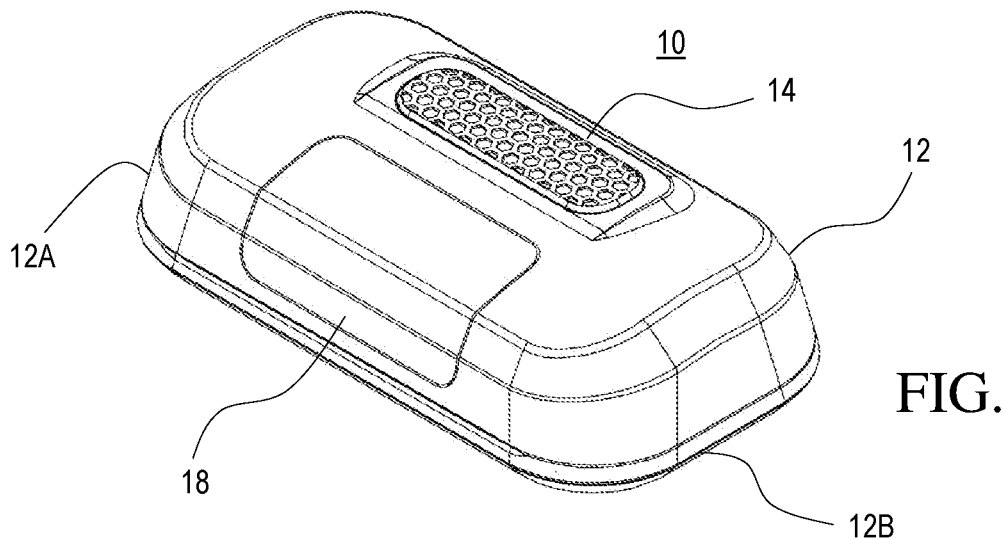
FIG. 1A shows an isometric view of a drug delivery pump having safety integrated insertion mechanisms, according to one embodiment of the present invention.

As used herein to describe the insertion mechanisms, drug delivery pumps, or any of the relative positions of the components of the present invention, the terms "axial" or "axially" refer generally to a longitudinal axis "A" around which the insertion mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D".

As used herein, the term "glass" should be understood to include other similarly non-reactive materials suitable for use in a pharmaceutical grade application that would normally require glass, including but not limited to certain non-reactive polymers such as cyclic olefin copolymers (COC) and cyclic olefin polymers (COP).

The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure.

"Fluid" refers primarily to liquids, but can also include suspensions of solids dispersed in liquids, and gasses dissolved in or otherwise present together within liquids inside the fluid-containing portions of syringes.

As used herein, the term "pump" is intended to include any number of drug delivery systems which are capable of dispensing a fluid to a user upon activation. Such drug delivery systems include, for example, injection systems, infusion pumps, bolus injectors, and the like.

According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring.

The novel devices of the present invention provide insertion mechanisms with integrated safety features and drug delivery pumps which incorporate such insertion mechanisms. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pump, insertion mechanism, and their respective components are described further herein with reference to the accompanying figures. The devices described herein may be configured for delivery of controlled substances and may further include features that prevent so-called "run-away" delivery of medicament. When delivering controlled substances, this may be an important safety feature to protect the patient. For example, some medicaments, such as insulin, can be dangerous, and potentially even deadly, when administered in too large a quantity and/or at too rapid of a rate. By providing such automatic safety stop mechanisms, the safety of the patient may be ensured.

Figure 1B:
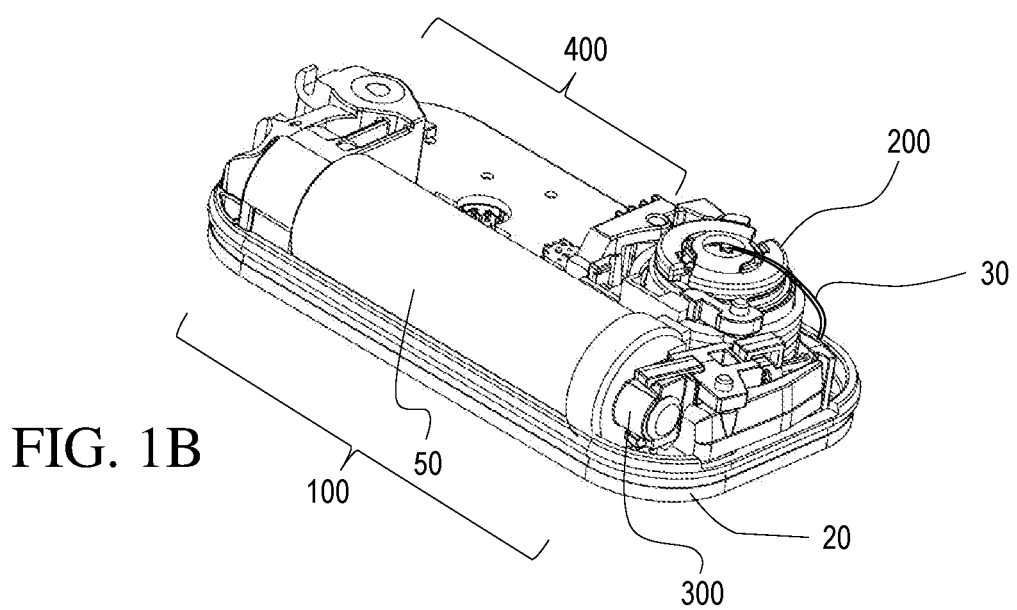
FIG. 1B shows an isometric view of the interior components of the drug delivery pump shown in FIG. 1A.
Figure 1C:
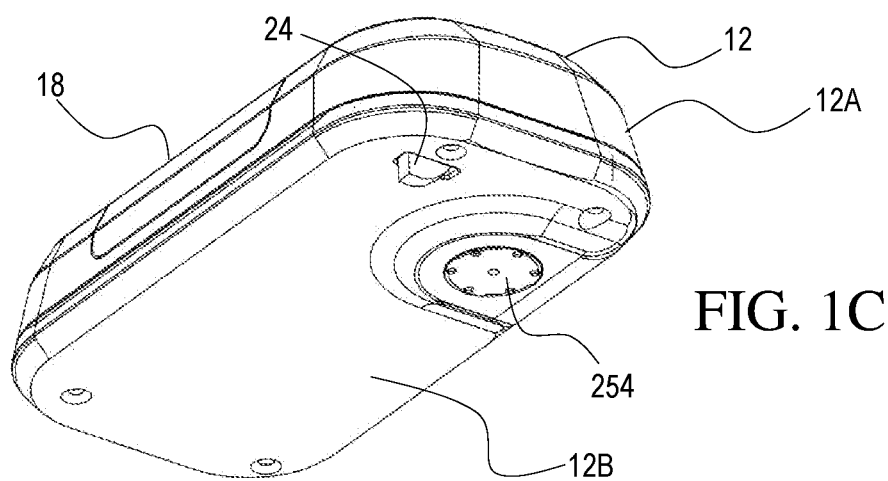
FIG. 1C shows an isometric view of the bottom of the drug delivery pump shown in FIG. 1A.

Drug Delivery Pump:

FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator (not shown), and a window 18. Window 18 may be any translucent or transmissive surface through which the operation of the drug pump may be viewed. As shown in FIG. 1B, the drug pump further includes assembly platform 20, drive mechanism 100 having drug container 50, insertion mechanism 200, fluid pathway connection 300 to establish a sterile fluid coupling between the drug container 50 and the needle or trocar in the insertion mechanism 200, and power and control system 400. One or more of the components of such drug pumps may be modular in that they may be, for example, pre-assembled as separate components and configured into position onto the assembly platform 20 of the drug pump 10 during manufacturing. Platform 20 may be a portion of housing 12, such as a portion of lower housing 12B, or, alternatively, may be a separate component.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as a status indicator and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator and a window 18. In other embodiments, one or more of the activation mechanism 14, the status indicator, the window 18, and combinations thereof may be provided on the upper housing 12A or the lower housing 12B such as, for example, on a side visible to the user when the drug pump 10 is placed on the target tissue. Housing 12 is described in further detail hereinafter with reference to other embodiments of the present invention.

The drug pump is configured such that, upon activation by a user by depression of the activation mechanism, the drug pump is initiated to: insert a fluid pathway into the user; enable, connect, or open necessary connections between a drug container, a fluid pathway connection, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 10) may be provided in one embodiment as a safety feature to ensure that the power and control system 400, or the activation mechanism, cannot be engaged unless the drug pump 10 is in contact with the target tissue. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a conductive-, capacitive- or impedance-based sensor which must detect tissue before permitting activation of the power and control system 400. In at least one embodiment, housing 12 is configured to at least partially prevent harmful matter from entering the drug pump. For example, the housing may be configured to restrict the passage of fluids into the drug pump. This may allow the device to be worn in the shower, while swimming, or during other activities. Use of an electrically based skin sensor may eliminate potential points of entry into the drug pump. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Figure 2A:
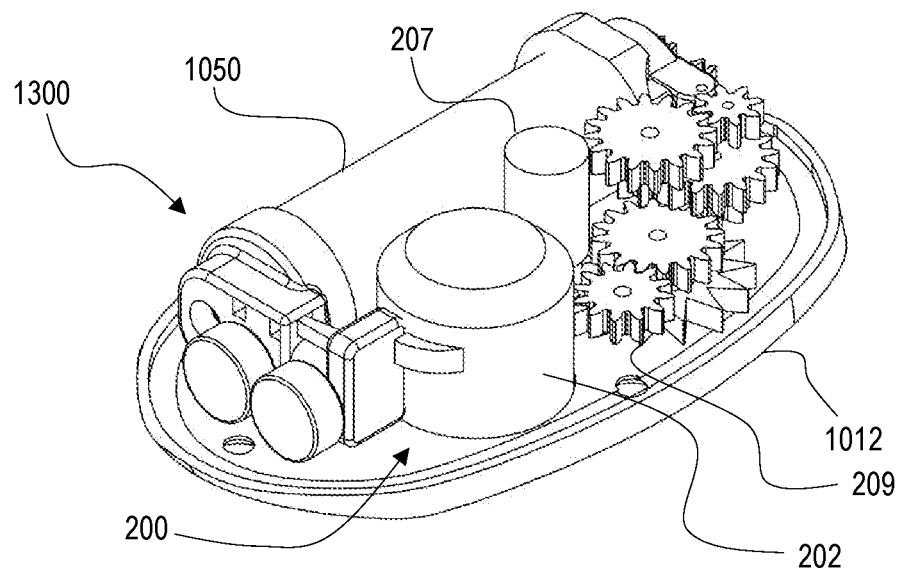
FIG. 2A shows an isometric view of the interior components of a second embodiment of a drug delivery pump.
Figure 2B:
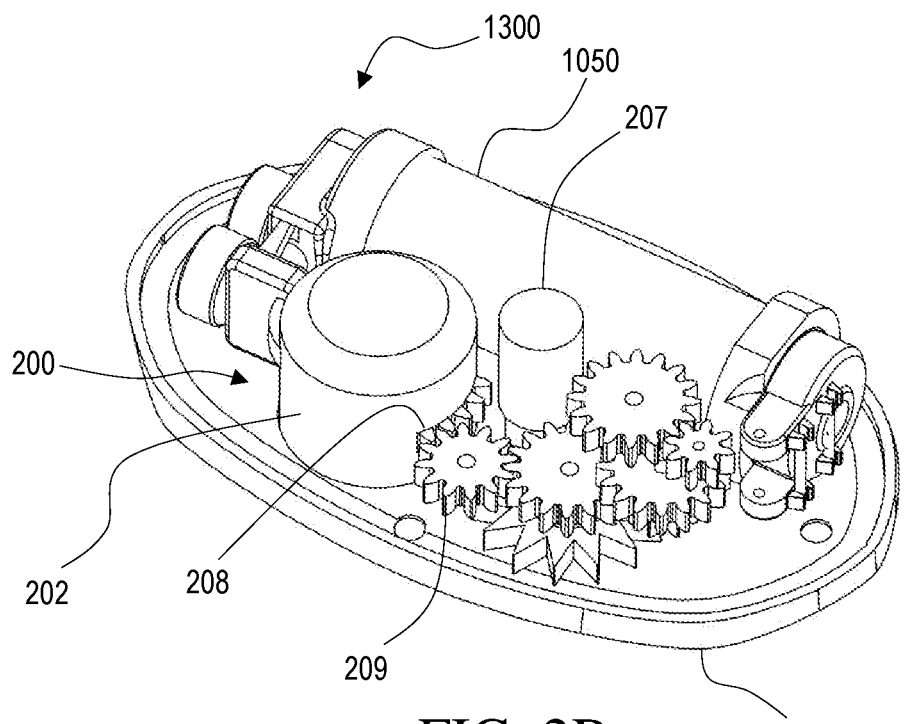
FIG. 2B shows a second isometric view of the interior components of the drug pump shown in FIG. 2A.

A second embodiment of a drug delivery pump 1300 is shown in FIGS. 2A-2B. As with the first embodiment, the drug container 1050 and insertion mechanism 200 may be disposed on an assembly platform or housing 1012. In this embodiment, one or more of the insertion mechanism 200, fluid pathway connection, and drug delivery drive mechanism are controlled by the motion of an actuator 207, such as a motor or solenoid, as well as the rotation of one or more gears 209. Additionally, or alternatively, an escapement mechanism may be used to control the rate of rotation of one or more gears. One of the gears may be engaged with teeth 208 of an insertion mechanism housing 202. As such, the rotation of one or more gears 209 of the gear train controls the rotation of the insertion mechanism housing and, thereby, the insertion of the needle into a target tissue. The operation of the insertion mechanism will be described further herein.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with a control arm to identify when the on-body sensor 24 and/or the activation mechanism 14 have been activated. The power and control system 400 may also interface with the status indicator of the pump housing 12, which may include a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator if device start-up checks provide no errors. After providing the ready-to-start status signal and, in an embodiment with the optional on-body sensor, if the on-body sensor remains in contact with the target tissue, the power and control system 400 will power the drive mechanism 100 to begin delivery of the drug treatment through the fluid pathway connection 300 and sterile fluid conduit 30 to the needle or cannula in the needle insertion mechanism 200. In a preferred embodiment of the present invention, the insertion mechanism 200 and the fluid pathway connection 300 may be caused to activate directly by user operation of the activation mechanism 14.

During the drug delivery process, the power and control system 400 is configured to provide a dispensing status signal via the status indicator. After the drug has been administered into the target tissue and, optionally, after the end of any additional dwell time, to ensure that substantially the entire dose has been delivered to the user, the power and control system 400 may provide an okay-to-remove status signal via the status indicator. This may be independently verified by the user by viewing the drive mechanism and drug dose delivery through the window 18 of the pump housing 12. Additionally, the power and control system 400 may be configured to provide one or more alert signals via the status indicator, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

The fluid pathway connection 300 includes a sterile fluid conduit 30, a piercing member, a connection hub, and a sterile sleeve. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the target tissue.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In a preferred embodiment, this connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid pathway connection and the drug container is desired. The sterile sleeve may be sterilized to ensure the sterility of the piercing member and the fluid pathway prior to activation.

Alternatively, or additionally, the sterility of the flow path may be preserved by one or more membranes or foils defining one or more sterile chambers of the fluid pathway connection. The membranes or foils may be pierced at the time of use of the drug pump by the piercing member or, alternatively, by an introducer member. In such an embodiment, the piercing member may be at least partially disposed within a lumen of the introducer member to prevent the piercing member from coming in contact with foreign substances.

The drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Drive Mechanism:

Referring now to FIG. 1B, the drive mechanism 100 includes drug container 50 having a cap 51, a pierceable seal, and a plunger seal. The drug container may contain a drug fluid, within a barrel between the cap and the plunger seal, for delivery through the insertion mechanism and drug pump into the target tissue. The drive mechanism may include any appropriate structure or mechanisms for advancing the plunger seal within the barrel. For example, the drive mechanism may further include one or more drive biasing members, one or more release mechanisms, and one or more guides. The components of the drive mechanism function to force a fluid from the drug container out through the pierceable seal or, preferably, through the piercing member of the fluid pathway connection for delivery through the fluid pathway connection, sterile fluid conduit, and insertion mechanism into the target tissue.

In one embodiment, the fluid stored in the drug container includes insulin. The fluid may include insulin of any concentration including U-100, U-300, and U-500.

The drive mechanism may further include one or more electrical contacts located on corresponding components which, upon contact between electrical contacts, are capable of continuing an energy pathway or otherwise relay a signal to and/or from the power and control system 400. Such signals may be transferred across one or more interconnects. Such components may be utilized within the drive mechanism to measure and relay information related to the status of operation of the drive mechanism, which may be converted by the power and control system 400 into tactile, auditory, and/or visual feedback to the user.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The translation of the plunger seal may be controlled, restricted, or metered by features of the drive mechanism 100. The fluid pathway connection is connected through the pierceable seal prior to, concurrently with, or after activation of the drive mechanism to permit fluid flow from the drug container, through the fluid pathway connection, sterile fluid conduit, and insertion mechanism, and into the target tissue for drug delivery. In at least one embodiment, the fluid flows through only a conduit, a needle, and a cannula of the insertion mechanism, thereby maintaining the sterility of the fluid pathway before and during drug delivery. Such components and their functions are described in further detail hereinafter.

Figure 3A:
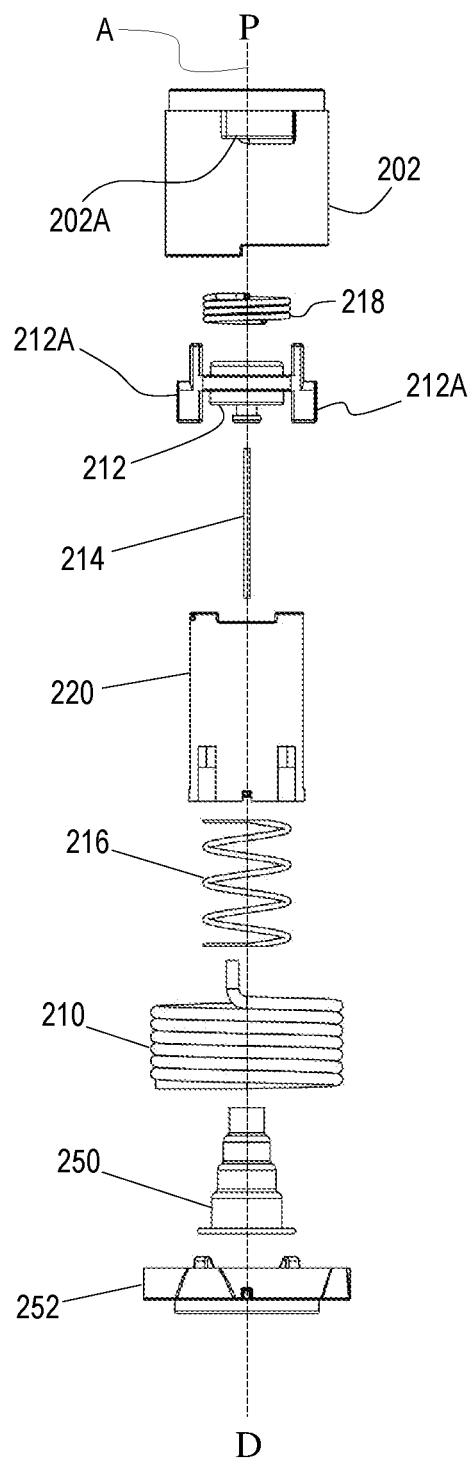
FIG. 3A shows an exploded view, exploded along an axis "A," of an insertion mechanism according to at least one embodiment of the present invention.
Figure 3B:
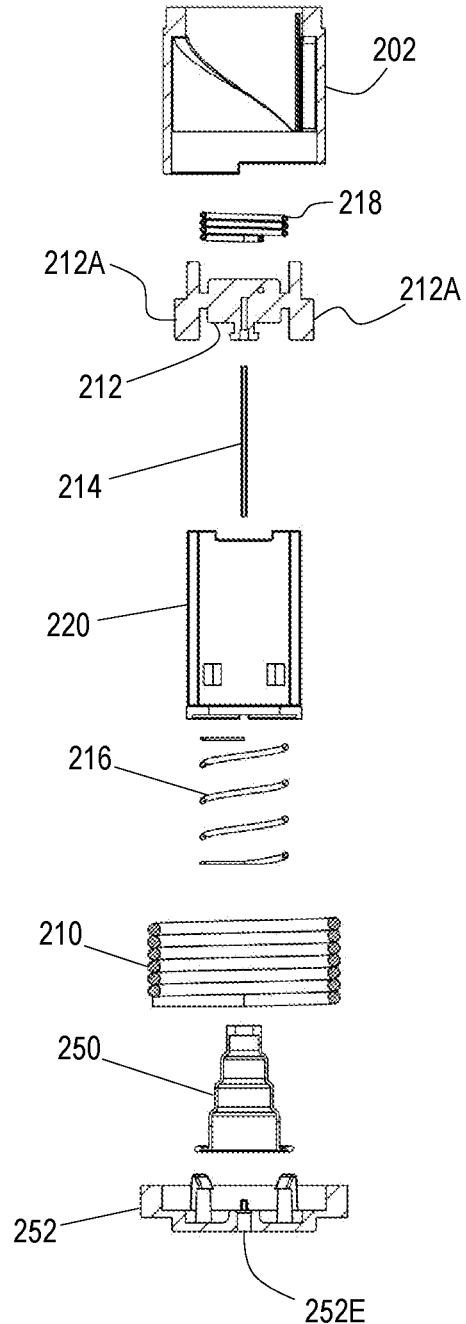
FIG. 3B shows a cross-sectional view of the exploded insertion mechanism of FIG. 3A.

Insertion Mechanism:

An exemplary insertion mechanism 200 is illustrated in exploded form in FIGS. 3A and 3B, while the individual components are illustrated in FIGS. 4A-4B and 5-7, and the assembled device and exemplary operation are illustrated in FIGS. 8A-10B. In this first embodiment, the insertion mechanism 200 includes an insertion mechanism housing 202 having one or more protrusions 202A, a base 252, and a sterile boot 250, as shown in the exploded view of FIGS. 3A and 3B. Base 252 may be connected to assembly platform 20 to integrate the insertion mechanism into the drug pump 10 (as shown in FIG. 1B). The connection of the base 252 to the assembly platform 20 may be, for example, such that the bottom of the base is permitted to pass-through a hole in the assembly platform 20 to permit direct contact of the base 252 to the target tissue. In such configurations, the bottom of the base 252 may include a sealing membrane 254 that, at least in one embodiment, is removable prior to use of the drug pump 10. Alternatively, the sealing membrane 254 may remain attached to the bottom of the base 252 such that the needle 214 pierces the sealing membrane 254 during operation of the drug pump 10.

As shown in FIGS. 3A and 3B, the insertion mechanism 200 may further include a rotational biasing member 210, a needle assembly including a needle hub 212 and a needle 214, a retraction biasing member 216, a sleeve 220, and a needle insertion mechanism (NIM) conduit 218. The NIM conduit 218 may connect to sterile fluid conduit 30 or to sterile access connection 300 to permit fluid flow through the NIM conduit 218, needle 214, and into the target tissue during drug delivery, as will be described in further detail herein.

As used herein, "needle" is intended to refer to a variety of needles including but not limited to conventional hollow needles, such as a rigid hollow steel needles. Upon assembly, the proximal end of needle 214 is maintained in fixed contact with hub 212, while the remainder of needle 214 is preferably located within sterile boot 250. The needle 214 may further pass-through base opening 252E (see FIG. 7).

In the illustrated embodiment, the sterile boot 250 is a collapsible or compressible sterile membrane that is in fixed engagement at a proximal end with the hub 212 and at a distal end with the sleeve 220 and/or base 252. In other words, the distal end of the sterile boot 250 is maintained in engagement with a fixed element, e.g., the sleeve 220/base 252, while the proximal end of the sterile boot 250 is maintained in engagement with an element moveable relative to the fixed element, i.e., the hub 212. In at least one embodiment, the sterile boot 250 is maintained in fixed engagement at a distal end between base 252 and sleeve 220. As will be understood by those of skill in the art, in other embodiments (not shown) sterile boot 250 may be maintained in fixed engagement at a distal end between base 252 and insertion mechanism housing 202.

Base 252 includes a base opening 252E through which needle 214 may pass during operation of the insertion mechanism, as will be described further below. Sterility of needle 214 is maintained by its initial positioning within the sterile portions of the insertion mechanism. Specifically, as described above, needle 214 is maintained in the sterile environment of the sterile boot 250. The base opening 252E of base 252 may be closed from non-sterile environments as well, such as by for example a sealing membrane 254.

Figure 4A:
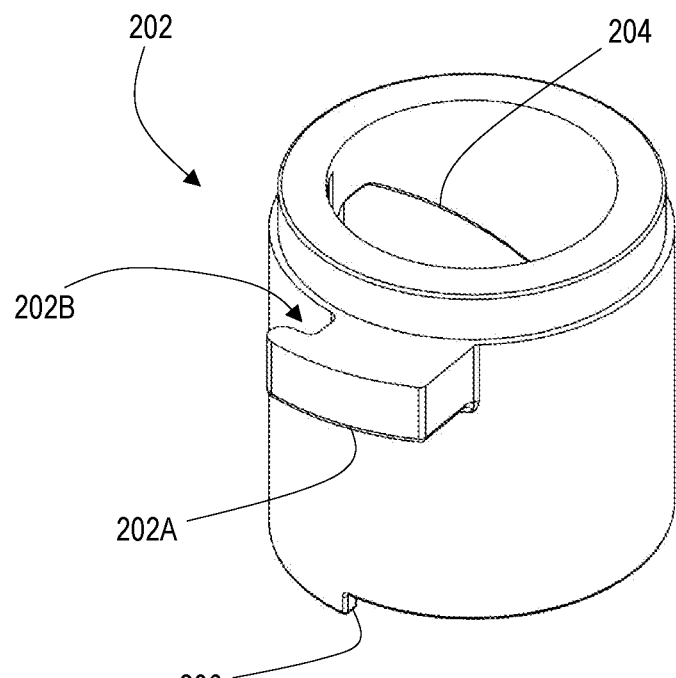
FIG. 4A shows an isometric view of an insertion mechanism housing according to at least one embodiment of the present invention.
Figure 4B:
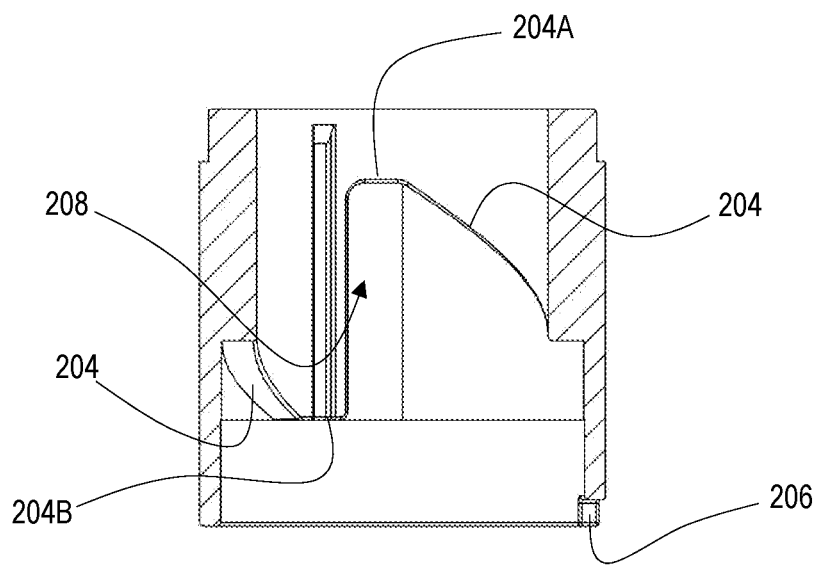
FIG. 4B shows a cross-section view of the insertion mechanism housing shown in FIG. 4A.

FIGS. 4A-4B and 5-7 show the components of the insertion mechanism, according to at least a first embodiment, in greater detail. As shown in FIGS. 4A-4B, insertion mechanism housing 202 may be a substantially cylindrical component having an inner chamber within which NIM conduit 218, hub 212, needle 214, sleeve 220, retraction biasing member 216, and sterile boot 250 are substantially disposed in an initial configuration (illustrated in FIGS. 8A and 8B). Guide surfaces 204 (as best seen in FIG. 4B) are located on the inner surface of housing 202 and are configured to interact with corresponding followers, here, extension arms 212A of hub 212. While two arms 212A are provided on the hub 212, and two guide surfaces 204 provided on the housing 202, it will be appreciated that a greater or lesser number of corresponding extension arms 212 and guide surfaces 204 may be provided, so long as the extension arms 212A and guide surfaces 204 are provided in pairs and configured for engagement. Guide surfaces 204 are ramped circumferentially around the inner surface of housing 202. That is, guide surfaces 204 each present an at least partially, radially disposed surface having a component that extends in both the axial and circumferential directions. As a result, as the housing 202 rotates relative to the hub 212, the movement of guide surfaces 204 contacting the extension arms 212A causes or permits the hub 212 to axially translate either proximally or distally with respect to the initial position. As such, guide surfaces 204 function as cam surfaces which convert rotational motion of housing 202 to axial translation of hub 212. In other words, and as will be described in further detail hereinafter, rotation of housing 202 is transferred to axial movement of hub 212 by interaction of guide surfaces 204 with extension arms 212A of hub 212.

In order to provide rotational movement to the housing 202, the housing 202 may further include one or more engagement surfaces 202B disposed for interaction with the rotational biasing member 210. In the illustrated embodiment, the housing 202 is provided with one or more protrusions 202A configured to engage a proximal end of rotational biasing member 210. Protrusion 202A may form an engagement surface 202B in the form of a recess in which the proximal end of rotational biasing member 210 may be disposed. In this way, unwinding and/or de-energizing of rotational biasing member 210 causes rotation of housing 202 about axis A.

Although the illustrated embodiments show the rotational biasing member engaging protrusion 202A, rotation of housing 202 and rotational biasing member 210 may be coupled in any way. For example, the rotational biasing member 210 may engage a slot, aperture, or bore in housing 202. As in the illustrated embodiment, rotational biasing member 210 may be located on the outside of housing 202 in a substantially concentric relationship. The distal end of the rotational biasing member may be engaged with base 252 or another axially-stationary feature of drug pump 10 such that movement of the distal end of rotational biasing member 210 is restricted.

Additionally, protrusion 202A, or another feature of housing 202, may further contact a portion of the sterile access connection during rotation of housing 202. This contact, in conjunction with rotation of housing 202, may be used to initiate the piercing of the pierceable seal and thereby allow the contents of the drug container to flow through the conduit.

Figure 5:
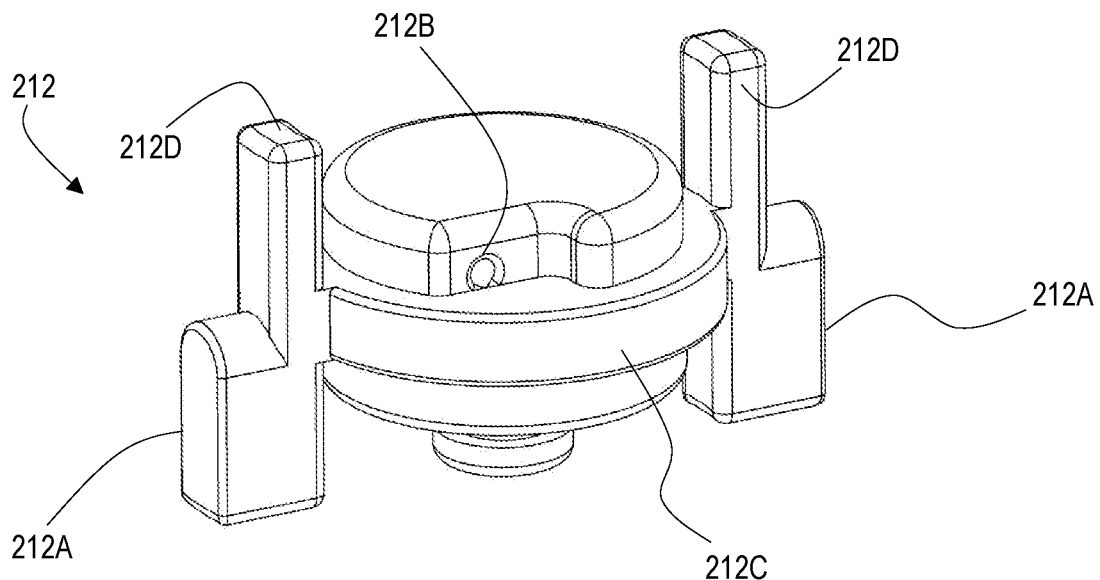
FIG. 5 shows an isometric view of a hub according to at least one embodiment of the present invention.

Hub 212, as seen in FIG. 5, includes extension arms 212A, as described above, extending from a central body portion 212C. It further includes aperture 212B configured to receive a portion of NIM conduit 218. Aperture 212B allows NIM conduit 218 to be in fluid communication with needle 214 for delivery of the fluid drug to the target tissue. Needle 214 is securely engaged with hub 212 by bonding, press-fit or any other means known to one skilled in the art.

Figure 6:
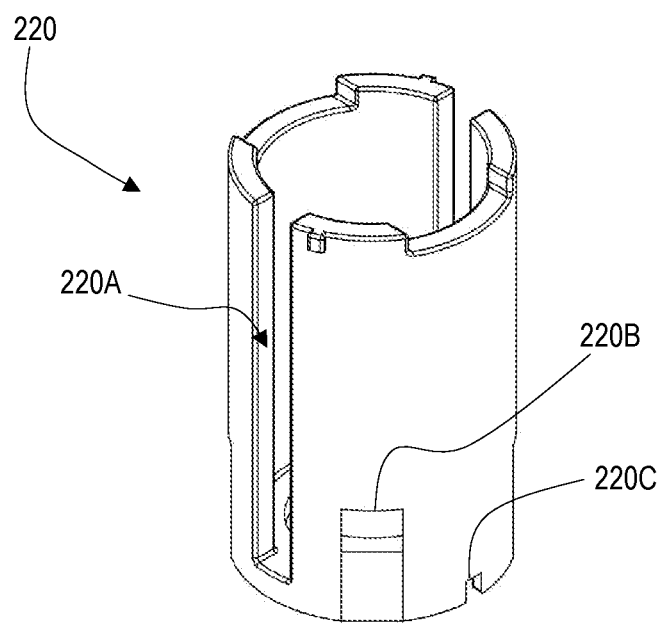
FIG. 6 shows an isometric view of a sleeve according to at least one embodiment of the present invention.

The central body portion 212C of the hub 212 is disposed to axially translate within sleeve 220, which is shown in greater detail in FIG. 6. In order to control the axial movement of the hub 212 relative to the sleeve 220, the hub 212 and sleeve 220 are provided with protrusions 212D and recesses configured to engage one another. In the illustrated embodiment, the protrusions 212D of the hub 212 are configured as part of the extension arms 212A, and the sleeve 220 includes slots 220A within which extension arms 212A of hub 212 are at least partially disposed during operation of the insertion mechanism. This interaction restricts the ability of hub 212 to rotate relative to the sleeve 220.

Figure 7:
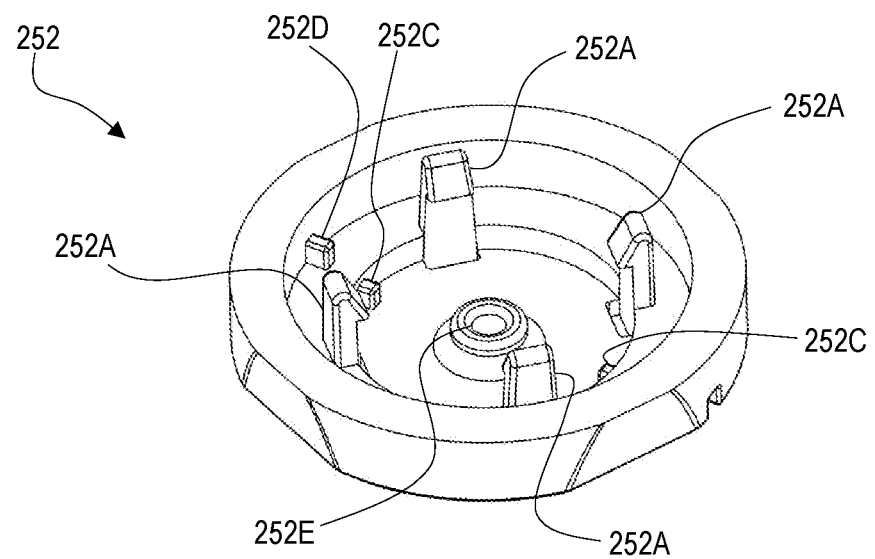
FIG. 7 shows an embodiment of a base of an insertion mechanism according to at least one embodiment of the present invention.

Sleeve 220 may further include structure configured to engage with the base 252 to restrict movement of the sleeve relative to the base 252. In the illustrated embodiment, the sleeve 220 includes one or more apertures 220B, which are configured to interface with flex arms 252A of base 252. During assembly, flex arms 252A engage apertures 220B, thereby restricting movement of sleeve 220 with respect to base 252. Base 252, as shown in FIG. 7, may further include one or more lower alignment members 252C configured to engage one or more alignment notches 220C of sleeve 220. This engagement aligns sleeve 220 to base 252 and further limits rotation of sleeve 220 with respect to base 252. Base 252 may also include one or more upper alignment members 252D configured to engage face 206 of housing 202 during installation, thereby positioning housing 202 with respect to base 252.

Figure 8A:
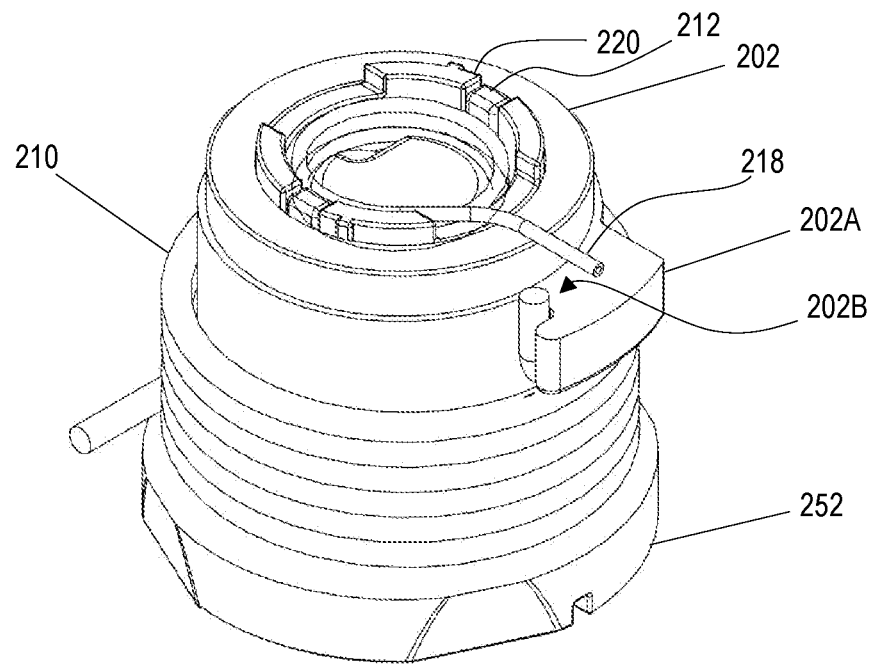
FIG. 8A shows an isometric view of an insertion mechanism according to at least one embodiment of the present invention in an initial configuration.
Figure 8B:
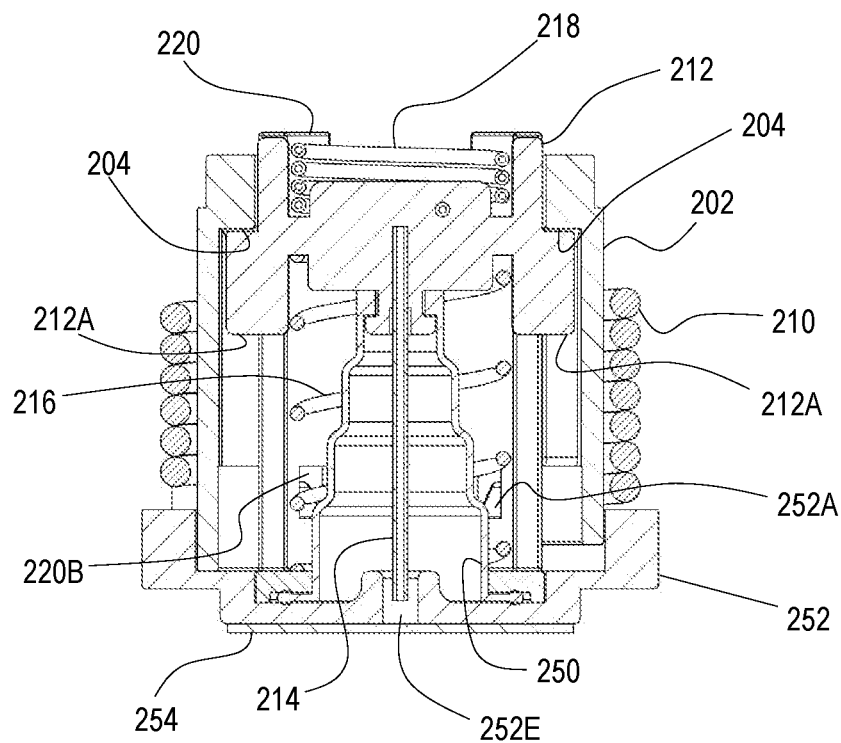
FIG. 8B shows a cross-sectional view of the insertion mechanism of FIG. 8A in an initial configuration.

The operation of the insertion mechanism is described herein with reference to the above components, in view of FIGS. 8-10. FIG. 8A shows an isometric view and FIG. 8B shows a cross-sectional view of the insertion mechanism, according to at least one embodiment of the present invention, in a locked and ready to use stage. The proximal end of rotational biasing member 210 is disposed on engagement surface 202B of housing 202 and rotational biasing member 210 is in an energized state. In this initial position, hub 212 is in a retracted, proximal position such that needle 214 does not extend past opening 252E of base 252. Sterile boot 250 is in an extended configuration with one end engaged with hub 212 and the other engaged with sleeve 220 and base 252. Extension arms 212A of hub 212 are located within or substantially adjacent to proximal portion 204A of guide surfaces 204 (see FIG. 4B). Coiled fluid NIM conduit 218 may be located proximally to hub 212. Fluid NIM conduit 218 may be connected at one end to hub 212, allowing fluid drug contents to pass from the drug container 50 to needle 214 for delivery to the target tissue.

In this embodiment, retraction biasing member 216 is disposed between the hub 212 and one or more axially-stationary elements of the insertion mechanism in a relatively decompressed and/or de-energized state. Here, the axially-stationary element is a portion of the sleeve 220. It will be appreciated, however, that the axially-stationary elements may include alternate components, such as, for example, the base 252, or a combination of two or more such axially-stationary elements.

It will further be appreciated that the retraction biasing member may be alternately disposed, and may include any appropriate type of retraction biasing member. For example, in an alternate embodiment, the retraction biasing member may include a tension spring, as opposed to a compression spring. In such an embodiment, the retraction biasing member may be disposed proximally to the hub 212 and coupled to the hub and an axially-stationary member in a de-energized state such that axial translation of the hub 212 in a distal direction energizes the tension spring.

As will be understood by those of skill in the art, insertion mechanism 200 may be held in this initial configuration by interaction with other components of drug pump 10. For example, drug pump 10 may include a NIM activation mechanism. The NIM activation mechanism may be initiated or activated by depression of activation member 14. Alternatively, the NIM activation mechanism may include a separate member configured for activation by the user. By way of example, activation member 14 may be engaged with a slide which, in an initial configuration, prevents rotation of housing 202 by interaction with protrusion 202A. Depression of trigger member 14 may displace the slide, disengaging the slide, or another component, from the protrusion 202A of housing 202, thereby allowing rotation of housing 202.

Figure 24A:
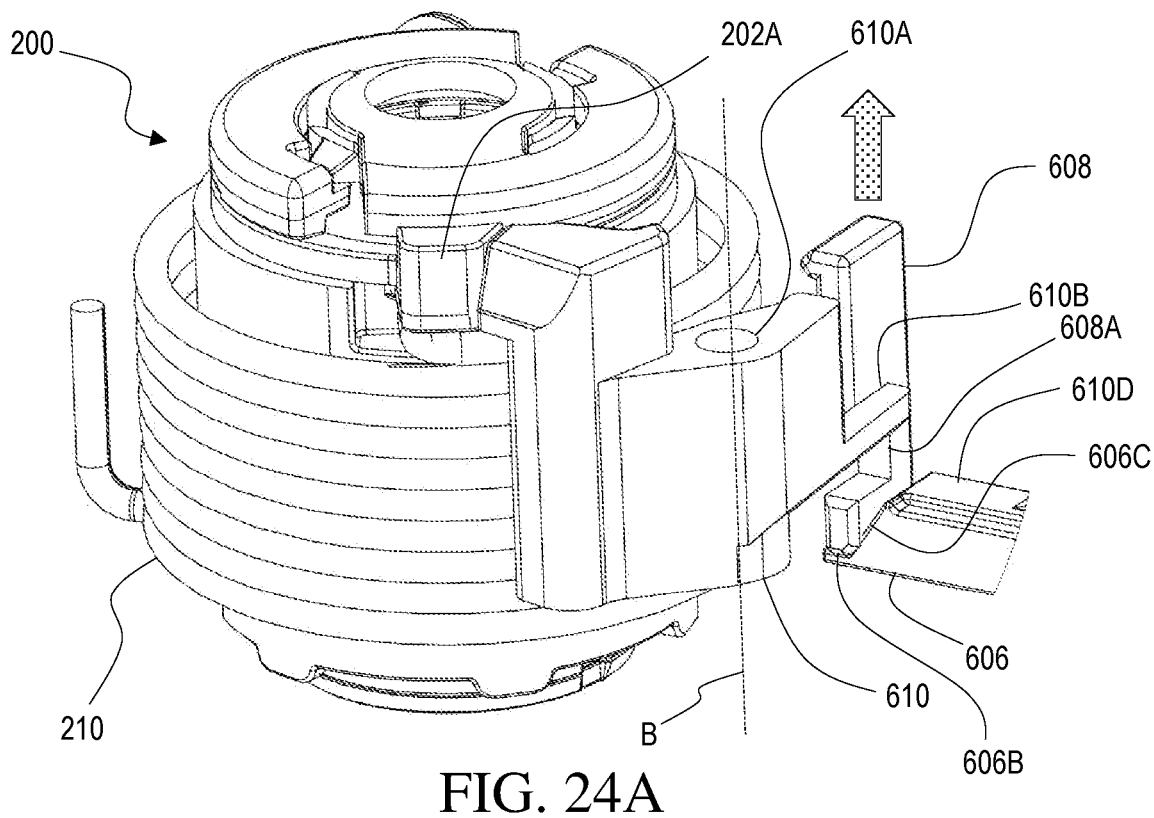
FIG. 24A is an isometric view of a NIM activation mechanism according to at least one embodiment of the present invention in an initial configuration.
Figure 24B:
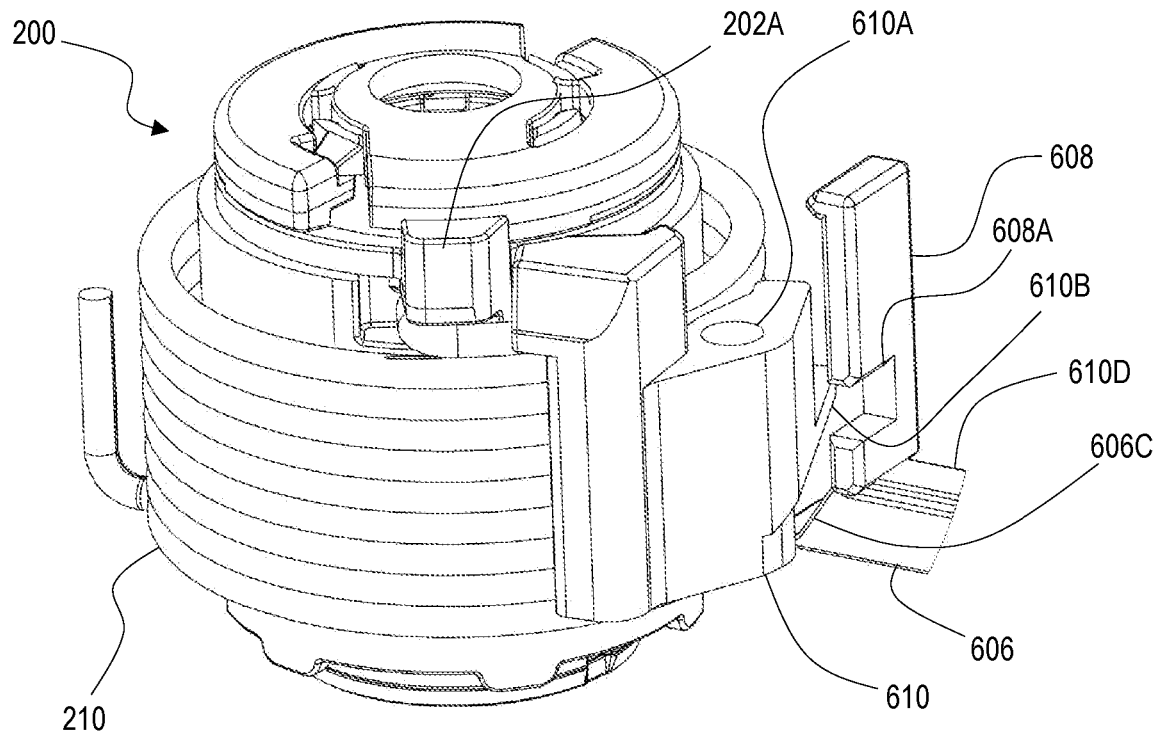
FIG. 24B is an isometric view of the NIM activation mechanism of FIG. 24A in an activated configuration.

One example of a NIM activation mechanism is shown in FIGS. 24A-24B. The NIM activation mechanism includes: a throw arm 606, a NIM interlock 608, and a NIM retainer 610. Initially, as shown in FIG. 24A, the NIM retainer 610 is positioned such that the NIM retainer 610 is in contact with a protrusion 202A of the housing 202 such that the housing 202 is prevented from rotating about axis A, thereby preventing activation of the NIM 200. In the embodiment shown, the NIM retainer 610 is configured for rotational movement about axis B. The NIM retainer 610 may, for example, be mounted to the housing 12 at bore 610A. For example, a pin or shaft may be disposed in bore 610A around which the NIM retainer 610 may rotate. The pin or shaft may an integral portion of the housing 12 or, alternatively, may be a separate component. The NIM retainer 610 is initially prevented from rotating by contact between an arm 610B of the NIM retainer 610 with the NIM interlock 608. The NIM interlock 608 is initially in a first position in which it is in contact with or adjacent to a lower surface 606B of the throw arm 606.

Depression of the activation mechanism 14 causes translation of the throw arm 606. The ramped surface 606C of the throw arm 606 contacts the NIM interlock 608 and causes the NIM interlock 608 to translate in a direction substantially orthogonal to the direction of translation of the throw arm 606 (i.e., in the direction of the shaded arrow in FIG. 24A). FIG. 24B shows the position of the throw arm 606 and NIM interlock 608 after translation of the throw arm. As shown, in this configuration, the NIM interlock is positioned adjacent to or in contact with an upper surface 606D of the throw arm 606. The window 608A of the NIM retainer 608 is aligned with the arm 610B of the NIM retainer 610. Hence, as shown in FIG. 24B, the NIM retainer 610 is able to rotate about axis B.

In at least one embodiment, the NIM retainer 610 is biased to rotate by a biasing member. The biasing member may be, for example, a torsion spring. Rotation of the NIM retainer 610 causes the NIM retainer 610 to disengage the protrusion 202A of the housing 202. Hence, the NIM 200 is able to activate to insert a fluid path into a target. Alternatively, force applied to NIM retainer 610 by protrusion 202A causes rotation of NIM retainer 610.

In other embodiments, the NIM interlock 608 may directly engage a portion of the NIM 200, such as the protrusion 202A, to initially prevent activation of the NIM 200. Translation of the NIM interlock 608 in the direction orthogonal to the translation of the throw arm 606 may cause the NIM interlock 608 to disengage the NIM 200 and allow the NIM 200 to activate.

In another embodiment, the throw arm 606 is directly engaged with a portion of the NIM whereby translation of the throw arm 606 allows activation of the NIM 200.

In an alternative embodiment, shown in FIGS. 2A-2B, a portion of housing 202 may have gear teeth 208 configured to interact with a gear 209 which prevents rotation of the housing. In this configuration, the gear may be connected to a motor 207 which controls the rotation of the gear and therefore the housing. The housing may be able to be disengaged from the gear, thereby allowing free rotation of the housing in response to de-energizing of the rotational biasing member. Gear 209 may be connected to motor 207 through a gear train, the gear train controlling the relationship between rotation of motor 207 and gear 209. Additionally, or alternatively, an escapement mechanism may be used to control rotation of the gear train.

Figure 9A:
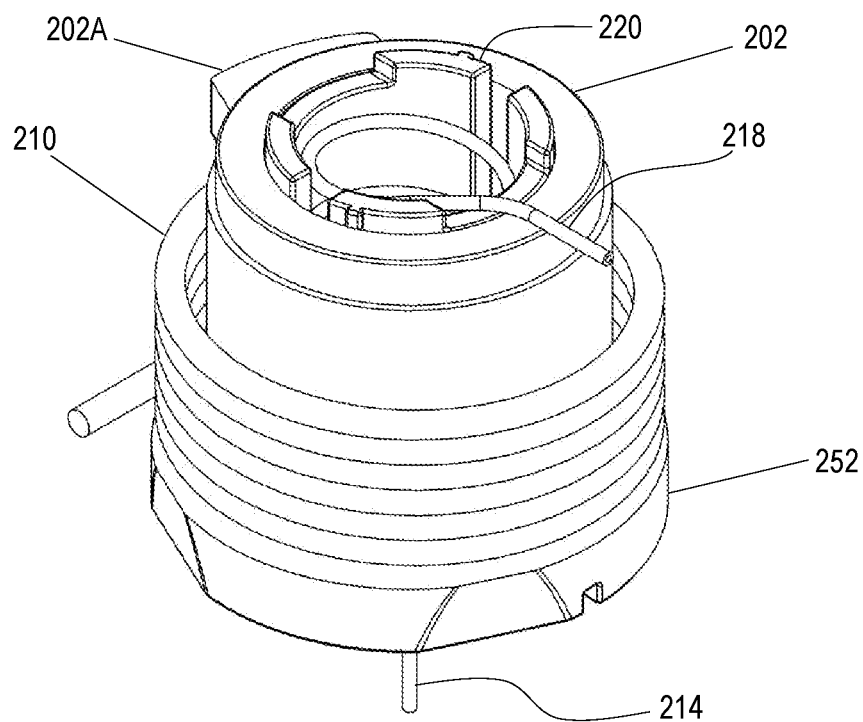
FIG. 9A shows an isometric view of the insertion mechanism of FIG. 8A in a needle inserted configuration.
Figure 9B:
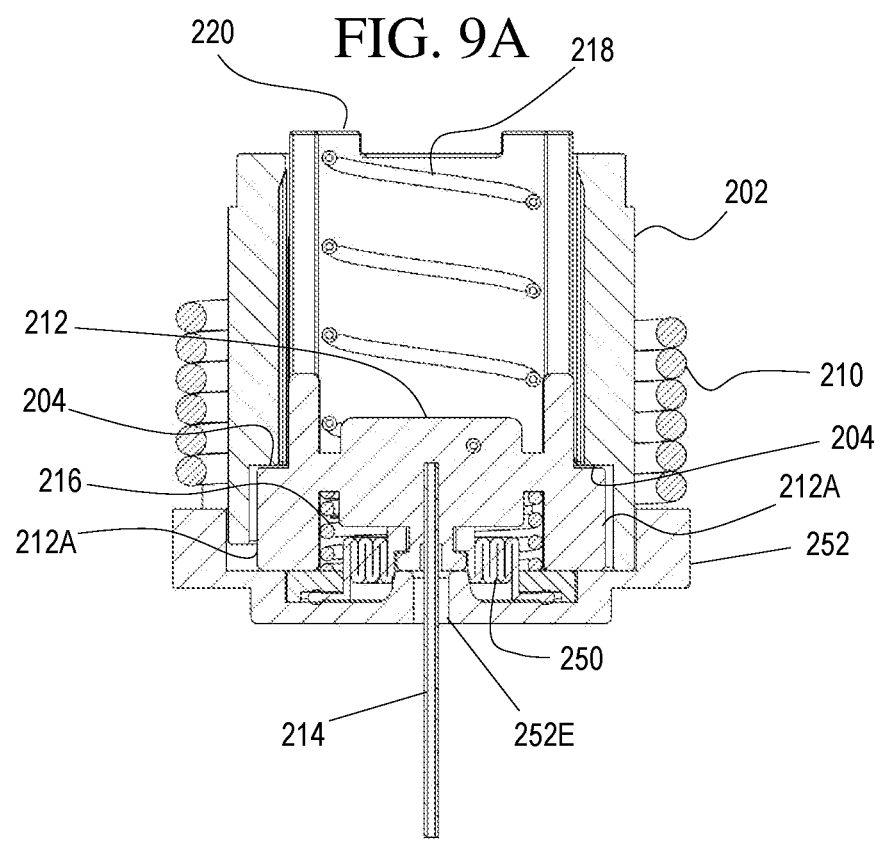
FIG. 9B shows a cross-sectional view of the insertion mechanism of FIG. 9A in a needle inserted configuration.

FIG. 9A shows an isometric view and FIG. 9B shows a cross-sectional view of an insertion mechanism in a needle inserted stage. As shown, unwinding and/or de-energizing of rotational biasing member 210 causes housing 202 to rotate about axis A (see FIG. 3A). As housing 202 rotates, contact of guide surfaces 204 with extension arms 212A of needle hub 212 causes hub 212 to translate in the distal direction. Force applied by rotation biasing member 216 may ensure that extension arms 212A maintain contact with guide surfaces 204. Hub 212 is prevented from rotating by interaction between extension arms 212A and slots 220A of sleeve 220. Sleeve 220 is coupled to base 252 by engagement of flex arms 252A with apertures 220B. As shown in FIG. 9B, sterile boot 250 is permitted to collapse as housing 202 rotates and hub 212 translates in the distal direction and inserts the needle 214 into the target tissue. At this stage, shown in FIG. 9B, needle 214 is introduced into the target tissue for drug delivery and extension arms 212A are in contact with distal portion 204B of guide surfaces 204. Due to the distal translation of hub 212, retraction biasing member 216 is compressed or energized. Rotation of housing 202 is preferably limited or stopped at a position in which guide surfaces 204 retain hub 212 in a distal position. Rotation of housing 202 may be stopped at this position by interaction between protrusion 202A and a stop component of drug pump 10. Alternatively, a stop component may interact with another portion of housing 202. Upon insertion of the needle 214, the fluid pathway from the NIM conduit 218 to the target tissue through the needle 214 is completed. As the fluid pathway connection is made to the drug container and the drive mechanism is activated, the fluid drug treatment is forced from the drug container through the fluid pathway connection and the sterile fluid conduit 218 into the needle 214 for delivery into the target tissue.

Figure 10A:
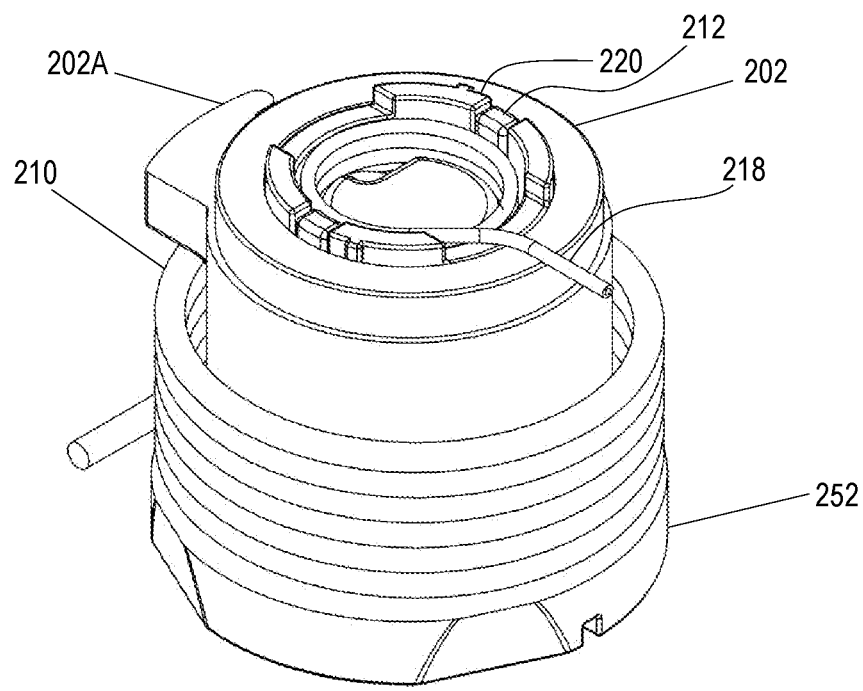
FIG. 10A shows an isometric view of the insertion mechanism of FIGS. 8A and 9A in a needle retracted configuration.
Figure 10B:
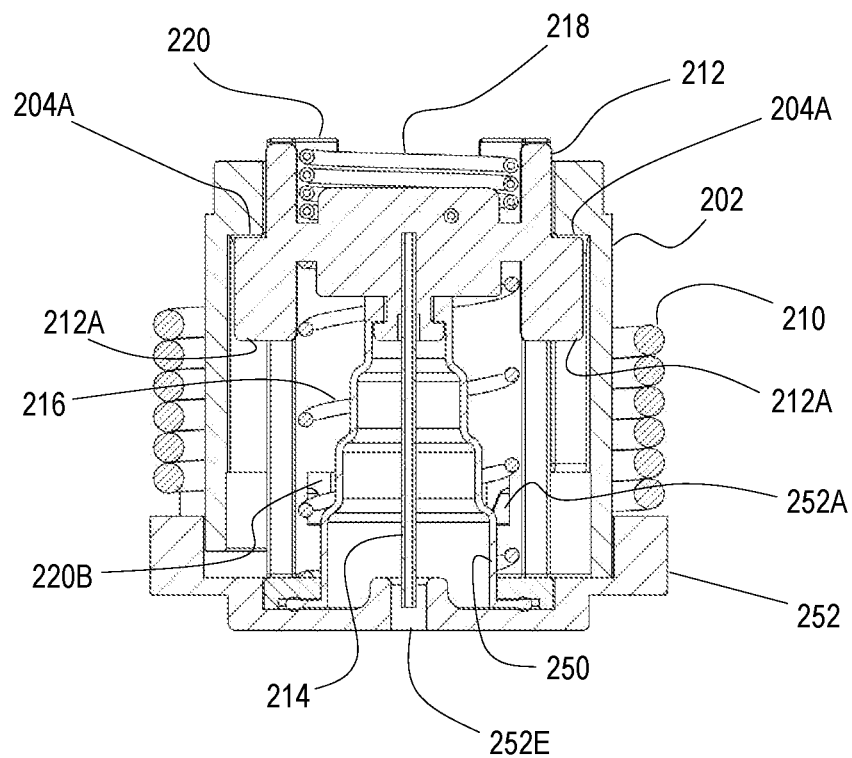
FIG. 10B shows a cross-sectional view of the insertion mechanism of FIG. 10A in a needle retracted configuration.

As shown in FIGS. 10A and 10B, upon completion of drug delivery, the needle 214 is retracted back (i.e., axially translated in the proximal direction) into the insertion mechanism housing 202. As the housing 202 continues to rotate, for example, under the force of the rotational biasing member 210, the secondary rotation of the housing 202 relatively positions the housing 202 and the hub 212 to permit the retraction biasing member 216 to at least partially de-energize. That is, additional rotation of housing 202 axially aligns the extension arms 212A of hub 212 with axial slot 208 of the housing 202 such that proximal translation of hub 212 within the housing 202 is no longer restricted by the guide surfaces 204. In this position, retraction biasing member 216, which has been energized as the hub 212 translated distally relative to the housing 202, is able to decompress or de-energize. Expansion of the retraction biasing member 216 translates hub 212, and needle 214 to which it is connected, axially in the proximal direction. Accordingly, activation of the insertion mechanism inserts the needle 214 into the target tissue, and sequentially retracts the needle 214 after completion of drug delivery or upon some other retraction initiation mechanism.

Figure 11:
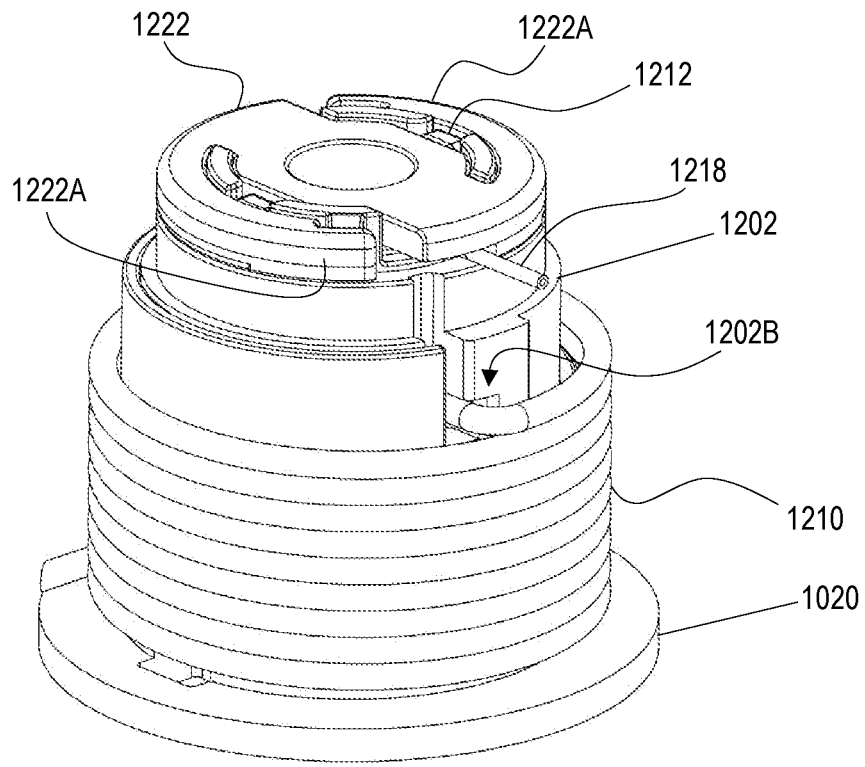
FIG. 11 shows an isometric view of an insertion mechanism according to at least one embodiment of the present invention.
Figure 12:
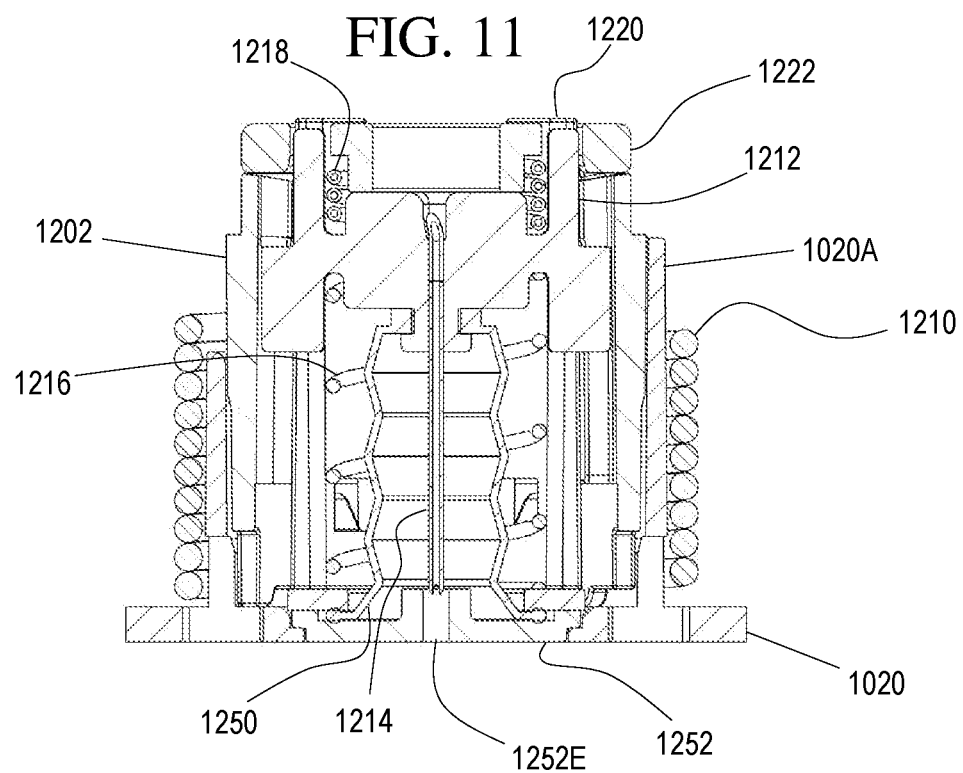
FIG. 12 shows a cross-sectional side view of the embodiment of FIG. 11.
Figure 13:
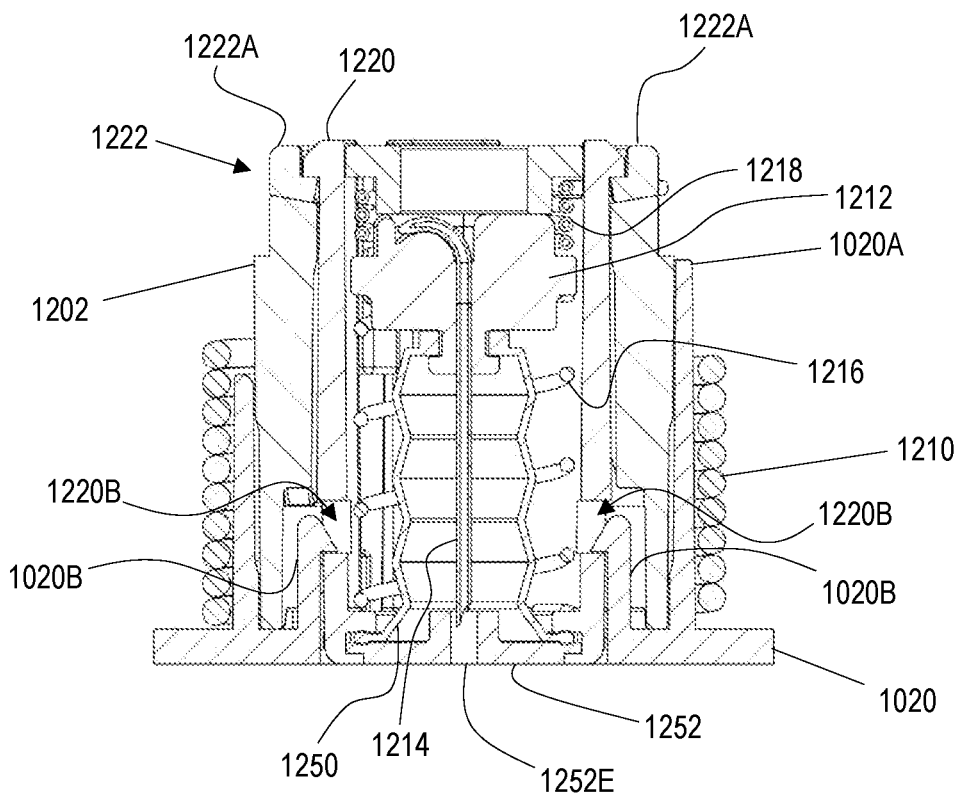
FIG. 13 shows a cross-sectional front view of the embodiment of FIG. 11.

FIGS. 11-13 show another embodiment of an insertion mechanism. For ease of understanding, structures in this embodiment are identified by the reference numbers utilized for similar structures in the first disclosed embodiment prefaced by the number "1". That is structures are identified by "1XXX" wherein the "XXX" refers to similar structures in the first embodiment. Accordingly, in the absence of a specific discussion below with regard to a reference number shown in FIGS. 11-13, those of skill in the art will understand that structures identified by reference numbers "1XXX" refer to the same or similar structures as discussed with regard to the first embodiment.

As shown in FIG. 11, one end of the rotational biasing member 1210 is disposed along an engagement surface in the form of a recess 1202B formed in the housing 1202 of the insertion mechanism. By engaging the housing 1202 in this way the requirement for a protrusion extending outwardly from the housing is eliminated, thereby allowing the overall size of the insertion mechanism to be reduced.

Further, as shown in FIG. 12 the sterile boot 1250 may be configured in an "accordion" configuration, which may allow the diameter of the sterile boot 1250 to be less than that of the sterile boot shown in previous embodiments.

It may also be seen in FIG. 12, the base portion of the insertion mechanism may include base 1252, through which base opening 1252E extends, and surrounding platform 1020. As may be seen in FIG. 12, the base 1252 and platform 1020 may have engaging structures that maintain the relative positions of the base 1252 and the platform 1020. Platform 1020 may additionally have one or more locating structures, such as upwardly extending boss 1020A, that aid in locating and retaining the needle insertion mechanism. The rotational biasing member 1210 may be positioned around the outside of boss 1020A and may engage one or more of the stationary structures, such as base 1252, platform 1020, or sleeve 1220. In this way, as energy is released from the rotational biasing member 1210, the housing 1202 rotates, as described above.

The needle insertion mechanism may also include cap 1222. The cap may engage the sleeve 1220 and act to retain the components of the needle insertion mechanism in place. Specifically, the cap may retain the conduit 1218, which is fluidly coupled to needle 1214 by way of hub 1212, in position within sleeve 1220. It is noted that the retraction biasing member 1216 bears against a lower surface of the hub 1212. The cap 1222 may be coupled with the sleeve 1220 by any appropriate mechanism. For example, the cap 1222 may include one or more circumferential flex arms 1222A which, during installation, may flex outward in response to contact with protrusions of the sleeve 1220 (see FIG. 13). The flex arms 1222A may then return to their natural position and thereby be retained in place with respect to the sleeve as seen best in the cross-section view of FIG. 13. Also seen in FIG. 13, one or more flex arms 1020B of platform 1020 may engage apertures 1220B of the sleeve 1220. This engagement retains and positions the insertion mechanism with respect to platform 1020 and with respect to the drug pump. The stages of operation of this embodiment may be substantially similar to those described above (i.e., de-energizing of the rotational biasing member leads to insertion of the needle and de-energizing of the retraction biasing member leads to retraction of the needle).

An additional embodiment of a needle insertion mechanism is shown in FIGS. 14A-16B. In this embodiment, utilizing a rigid needle 2214 to assist in placement, a flexible cannula 2260 is inserted into the target tissue for delivery of medicament. The rigid needle 2214 may be a hollow needle or a solid trocar. In the embodiment shown in FIGS. 14A-14C, a hollow needle is used to insert the cannula 2260. For ease of understanding, structures in this embodiment are identified by the reference numbers utilized for similar structures in the first disclosed embodiment prefaced by the number "2", or as in the second disclosed embodiment, changing the reference number from "1XXX" to "2XXX". That is structures are identified by "2XXX" wherein the "XXX" refers to similar structures in the first embodiment, or the similar structures in the second embodiment identified by "1XXX". Accordingly, in the absence of a specific discussion below with regard to a reference number shown in FIGS. 14A-16B, those of skill in the art will understand that structures identified by reference numbers "2XXX" refer to the same or similar structures as discussed with regard to the first or second embodiments. For the purpose of clarity, a platform is not shown in FIGS. 14A-14C, one of skill the art will understand that a platform similar to that illustrated in previous embodiments may be used in this and subsequent embodiments.

Figure 14A:
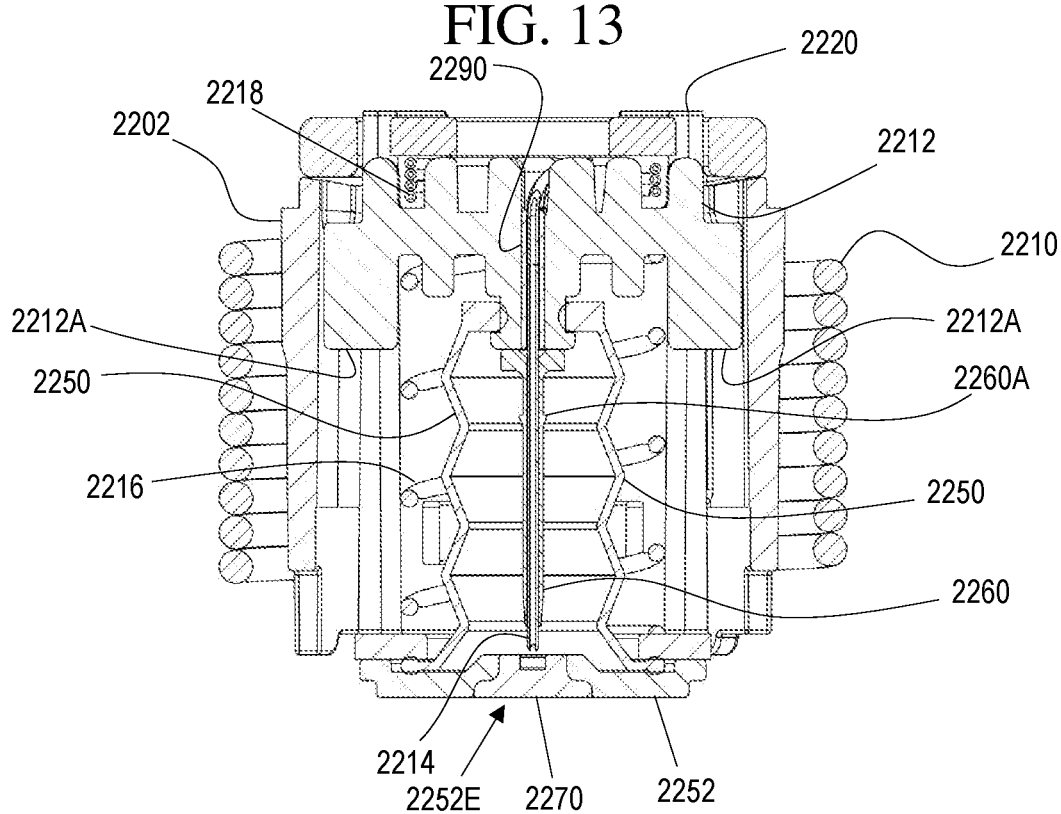
FIG. 14A shows a cross-sectional view of an insertion mechanism according to at least one embodiment of the present invention in an initial configuration.
Figure 14B:
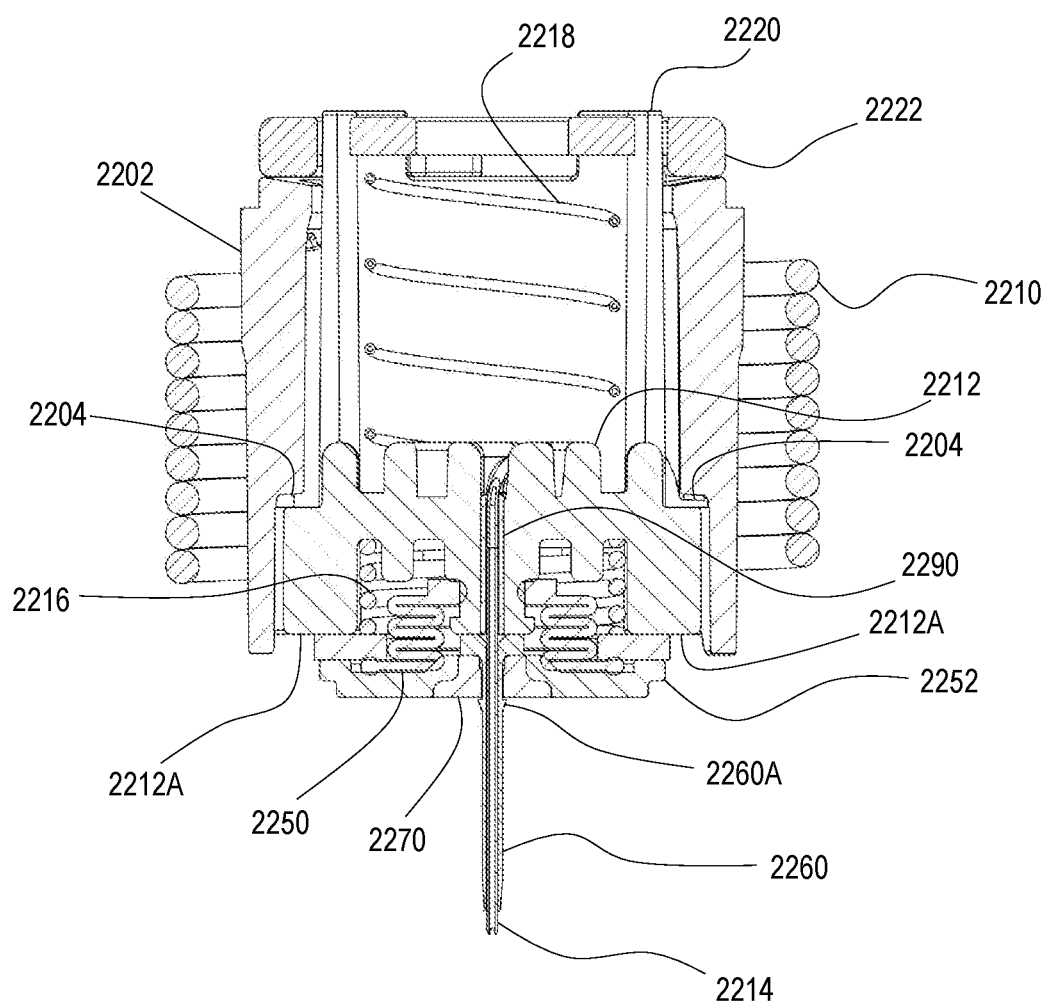
FIG. 14B shows a cross-sectional view of the insertion mechanism of FIG. 14A in an inserted configuration.

FIG. 14A shows the insertion mechanism in an initial configuration prior to activation. In the initial configuration, flexible cannula 2260 is disposed such that the rigid needle 2214 passes through the lumen of the flexible cannula. Additionally, the proximal end of flexible cannula 2260 is in contact with, or is in proximity to, needle hub 2212. As shown, the cannula 2260 is initially disposed within sterile boot 2250 and septum 2270 is disposed in aperture 2252E in base 2252. In this way, needle 2214 and cannula 2260 are thereby maintained in an aseptic condition. The cannula may be engaged with the needle by press-fit, bonding, or any other joining method. The needle may be further retained and/or located in the hub 2212 by retainer 2290. Upon activation of the insertion mechanism, rotation of housing 2202, caused by de-energizing of rotational biasing member 2210, causes needle hub 2212 to translate in the distal direction. This translation may be guided by contact of followers/arms 2212A of hub 2212 with guide surfaces 2204 on the interior of housing 2202 as described above and as shown in FIGS. 15A-15B. Translation of needle hub 2212 causes needle 2214 and cannula 2260 to also translate in the distal direction, pierce septum 2270, and be inserted into the target tissue. FIG. 14B shows the insertion mechanism at the completion of the insertion step.

Figure 14C:
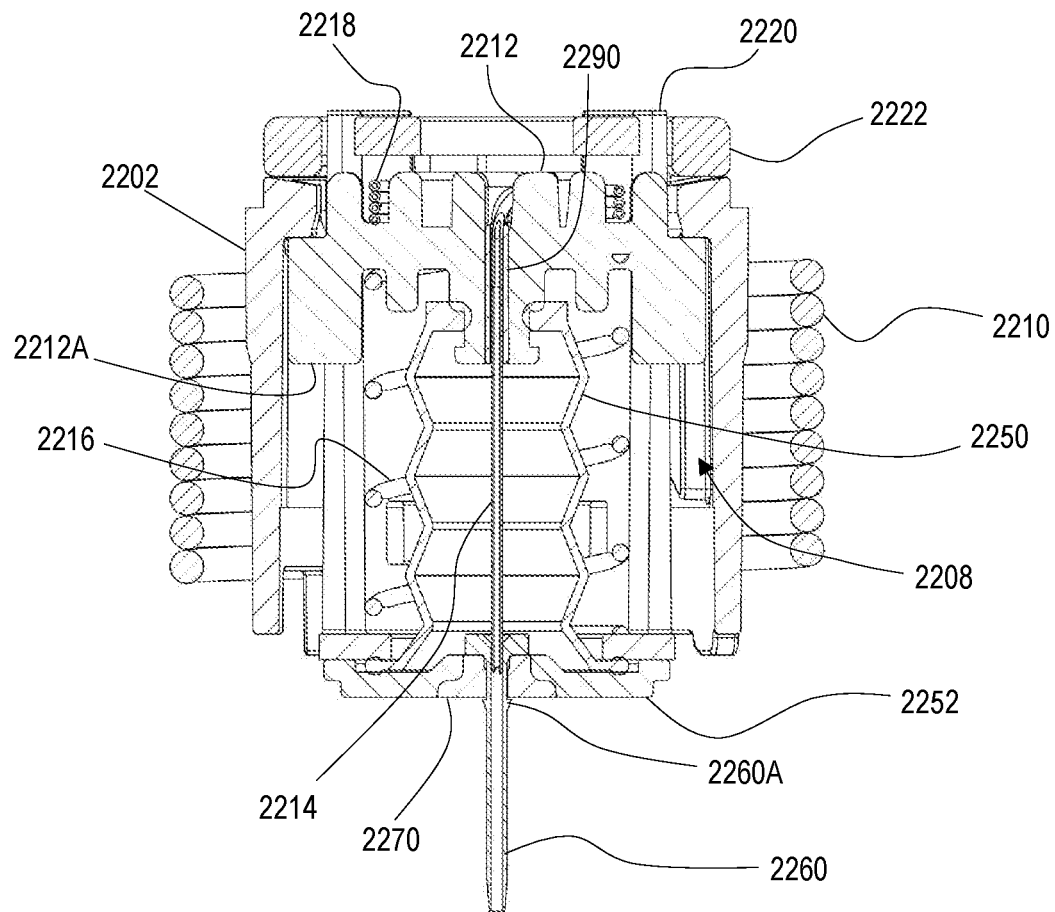
FIG. 14C shows a cross-sectional view of the insertion mechanism of FIG. 14A in a delivery configuration.
Figure 15A:
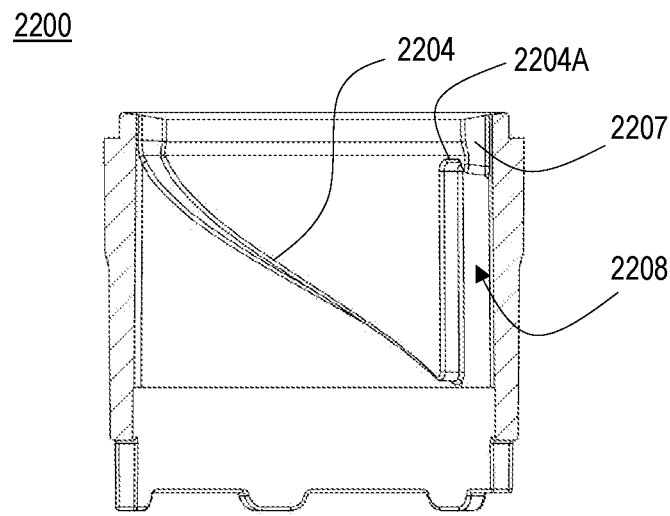
FIG. 15A shows a cross-sectional side elevational view of an insertion mechanism housing according to at least one embodiment of the present invention.
Figure 15B:
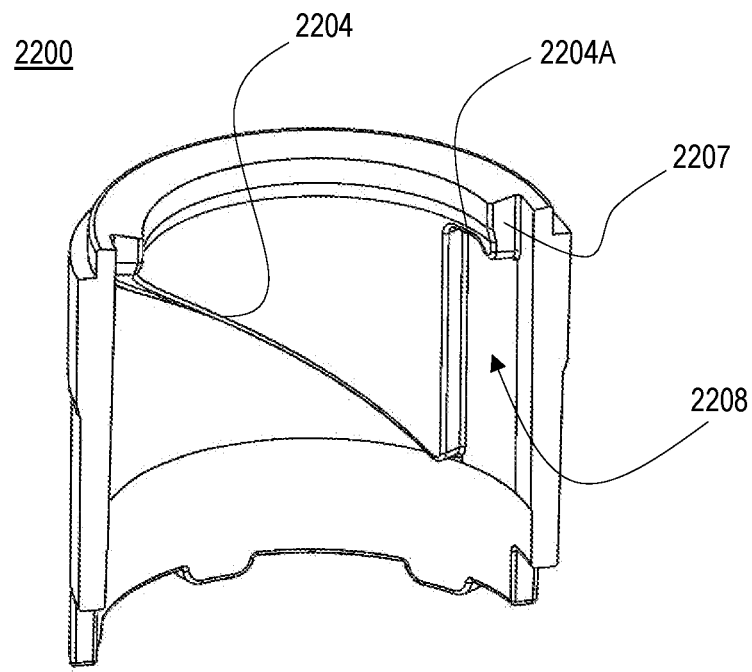
FIG. 15B shows a cross-sectional isometric view of the insertion mechanism housing of FIG. 15A.

As the housing 2202 continues to rotate, for example, under the force of the rotational biasing member 2210, the secondary rotation of the housing 2202 relatively positions the housing 2202 and the hub 2212 to permit the retraction biasing member 2216 to at least partially de-energize. In other words, this further rotation of housing 2202 aligns extension arms 2212A of hub 2212 with axial slot 2208 of housing 2202. In this position, retraction biasing member 2216 is able to de-energize or decompress, causing hub 2212 and needle 2214 to translate in the proximal direction. FIG. 14C shows the insertion mechanism at the completion of this step. Cannula 2260 is maintained in the inserted position and in the target tissue and needle 2214 is at least partially disposed within the cannula. This creates a fluid path through conduit 2218, needle 2214, and cannula 2260 for delivery of the medicament to the target tissue. Because only the flexible cannula 2260 is disposed within the target tissue, the cannula 2260 may flex in response to movement. This may provide advantages in patient comfort. Barb 2260A of cannula 2260 may be configured to engage septum 2270 and thereby resist retraction of the cannula 2260 into the insertion mechanism. Optionally, the needle 2214 may be partially disposed in the target tissue when in this position.

In addition to the advantages described above, the insertion mechanisms described herein may also be capable of terminating flow of medicament to the target tissue by disconnecting the fluid path. This may be an important safety feature to protect the patient. For example, some medicaments, such as insulin, can be dangerous, and potentially even deadly, when administered in too large a quantity and/or at too rapid of a rate. By providing such automatic safety stop mechanisms, so-called "run-away" delivery of medicament may be prevented, thereby ensuring the safety of the patient. While the methods and associated structures for terminating flow may be discussed with regard to one or more specific insertion mechanisms disclosed herein, it will be appreciated that the method and associated structures may be utilized or adapted for any of the insertion mechanisms disclosed herein or within the spirit and scope of this disclosure.

An interruption in delivery of medicament to the target tissue may be triggered, for example, by an error in delivery of the medicament or by an input from the user. For example, the user may realize that they have already taken their drug dose and wish to pause or terminate drug delivery from the device. Upon such user input to the device, the delivery of the drug can be stopped and/or the fluid passageway through the needle or cannula may be terminated by retraction of the needle to its fully retracted position, as described below.

Additionally or alternatively, the device may pause or terminate drug delivery if it receives an error alert during operation. For example, if the drive mechanism is not functioning correctly, the needle insertion mechanism may be triggered to retract fully and terminate drug delivery to the target tissue to prevent over-delivery of a medication to the target tissue. This capability of the needle insertion mechanism provides a valuable safety feature for drug delivery to a user.

In some embodiments, retraction is activated upon removal of the drug pump from the target tissue. In other embodiments, retraction is activated if it is determined that an error has occurred in the delivery of the substances to the target tissue. For example, an occlusion of the drug delivery pathway which prevents the flow of medicament may be detected by a sensing function of the drug delivery pump. Upon the sensing of the occlusion an electrical or mechanical input may be used to initiate retraction of the needle.

Activating retraction of the needle may be accomplished through many mechanisms. For example, a termination mechanism may be provided on the outside of housing 12 which, when depressed or engaged by the user, activates retraction of the needle from the user's body. For example, in one embodiment, depressing or engaging the termination mechanism may allow housing 202 to rotate, hence allowing retraction biasing member 216 to expand and retract needle 214. Actuation of the termination mechanism may be spring assisted such that the travel and/or force required to depress the termination mechanism is reduced. Alternatively, or additionally, upon drive mechanism 100 reaching end-of-dose, an electrical or mechanical actuator may cause activation of retraction. For example, upon end-of-dose, an electrical connection may be made such that a current is applied to a nitinol component. Upon application of the current, the nitinol component's temperature rises. Because of nitinol's shape memory characteristics this component may be configured, upon an increase in temperature, to transform from a first configuration to a second configuration. In this second configuration, the nitinol component may allow or cause the actuation of the retraction of the needle by, for example, allowing rotation of housing 202.

Alternatively, or additionally, a sensor such as on-body sensor 24 may, when drug pump 10 is removed from the target tissue, cause or allow activation of the retraction of the needle. For example, when pump 10 is installed on the target tissue the position of on-body sensor 24 may prevent rotation of housing 202 to the retraction position. Upon removal from the target tissue a change in configuration of on-body sensor 24 may allow rotation. In another embodiment, a light sensor may be placed on drug pump 10 near to base opening 252. When drug pump 10 is in place on the user's body, light would be substantially blocked from entering the light sensor. Upon removal of drug pump 10 from the target tissue, light may be sensed by the light sensor and the light sensor may trigger an electromechanical actuator to allow or cause activation of retraction. In other embodiments, a pin-type press-fit interconnect is used to initiate retraction of the needle. The pin may be biased to at least partially protrude from housing 12 and be displaced upon placement of pump 10 on the user. When displaced, the pin may engage a female hole on a PCB which may be a part of power and control system 400. Upon removal of pump 10 from the user, the biased pin disengages the female PCB hole, thereby causing a signal to activate the retraction of the needle.

Retraction of the needle and/or cannula may further be initiated upon a failure and/or fault of drive mechanism 100. For example, the drive mechanism may include a tether which serves to meter or control the rate of delivery of the contents of drug container 50. The tension applied to, or sustained by, the tether may be monitored by one or more sensors. A reduction in the tension of the tether may be an indication that the tether is not properly metering or controlling the delivery of the medicament. The sensor may be a mechanical component or linkage which is in contact with a portion of the tether, the contact at least partially controlling the position and/or configuration of the sensor. In a response to a reduction in tension in the tether, the sensor transforms from a first position to a second position. This transformation may, directly or indirectly, cause retraction of the needle and/or cannula. The retraction may be caused by a purely mechanical action or, alternatively, may involve an electrical signal received and/or generated by power and control system 400.

In other embodiments, the sensor may be a strain gauge, load cell, force sensor or other sensor which is configured to measure and/or monitor the strain, load, or tension present in the tether. In these embodiments, the sensor is at least partially affixed to the tether and generates an electrical signal based on the tension of the tether. The electrical signal may vary in magnitude in proportion to the magnitude of tension in the tether. Alternatively, the signal may be either interrupted or initiated when the tension in the tether falls below or exceeds a specified magnitude. The signal may be monitored by the power and control system which, based on the presence, absence, or magnitude of the signal, may cause or allow the retraction of the needle and/or cannula.

In still other embodiments, a mechanical failure of the tether may directly cause an electrical signal to be initiated or interrupted. For example, the tether may be constructed, at least partially, from a conductive material. The tether may be in electrical communication with the power and control system. The mechanical failure of the tether may interrupt a current path through the tether and cause a change in the flow of current in one or more circuits. This change may initiate or allow the retraction of the needle and/or cannula.

Additionally, or alternatively, the position and/or velocity of one or more features of the drive system may be monitored by a sensor such as: an optical sensor, such as an encoder; a potentiometer; or a transducer. If the position and/or velocity of the monitored feature exceeds or falls below a specified threshold, the power and control system may initiate and/or allow retraction of the needle and/or cannula.

Figure 16A:
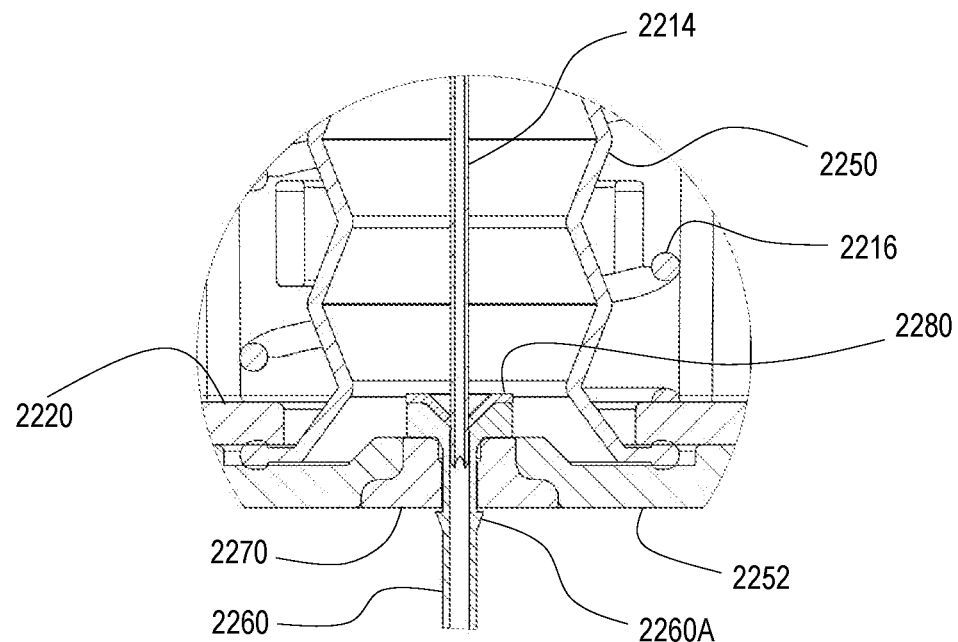
FIG. 16A is an enlarged, fragmentary cross-sectional view of the insertion mechanism of FIGS. 14A-14C, while in a delivery configuration.
Figure 16B:
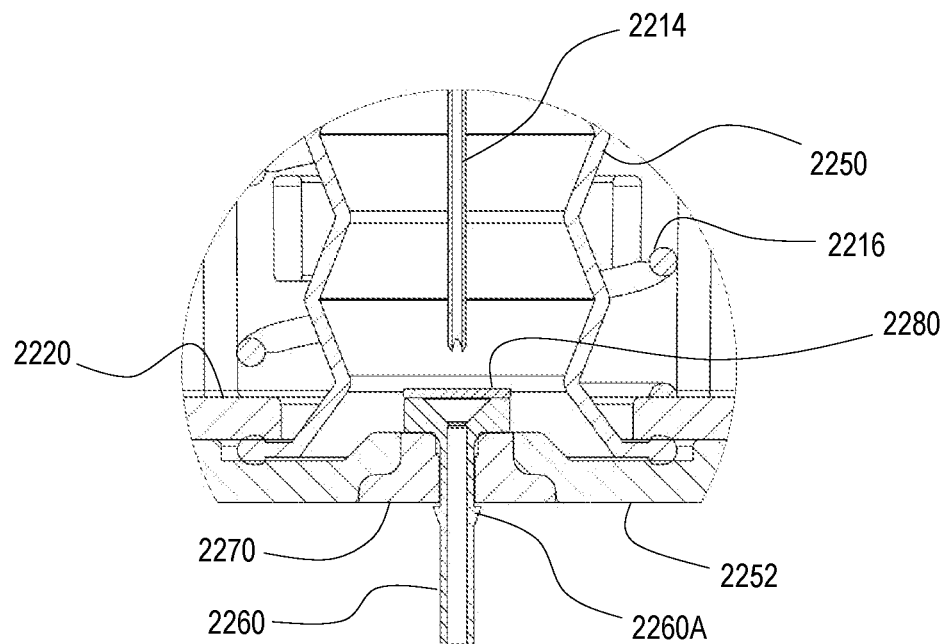
FIG. 16B is an enlarged, fragmentary cross-sectional view of the insertion mechanism of FIGS. 14A-14C, while in a retracted position

In one example, in the embodiment shown in FIGS. 14A-14C, flow of medicament to the target tissue can be terminated by retracting needle 2214 from cannula 2260. FIG. 16A shows a detail view of the needle 2214 in a delivery position. In this position, the needle 2214 is at least partially disposed within the cannula 2260, thereby creating a fluid path through the conduit, needle, and cannula and into the target tissue. FIG. 16B shows a detail view of a configuration in which the needle 2214 has been retracted such that it is no longer disposed within the cannula 2260. That is, as the housing 2200 is continued to rotate, for example, under the force of the rotation biasing member 2210, this tertiary rotation of the housing 2200 aligns the followers 2212A with retraction apertures 2207 in the housing 2200, allowing the retraction biasing member 2216 to further de-energize and move the needle 2214 to a fully retracted position. Because the needle 2214 is no longer disposed within the cannula 2260, a fluid path does not exist for delivery of medicament to the target tissue. Any additional fluid that passes through the conduit 2218 will be discharged through the needle 2214 to the interior of the drug pump, for example within sterile boot 2250. A barrier 2280 may be included to further prevent any medicament from entering cannula 2260 after retraction of the needle from the cannula. The barrier 2280 may be, for example, a septum which is pierced by the needle during assembly of the needle and cannula. Alternatively, the barrier 2280 may be a membrane or a clip which is displaced by the needle during assembly but which, upon retraction of the needle from the cannula, substantially covers the lumen of the cannula. A pressure differential within the cannula may also prevent the flow of medicament there-through after retraction of the needle, with or without the utilization of a barrier 2280.

Figure 25A:
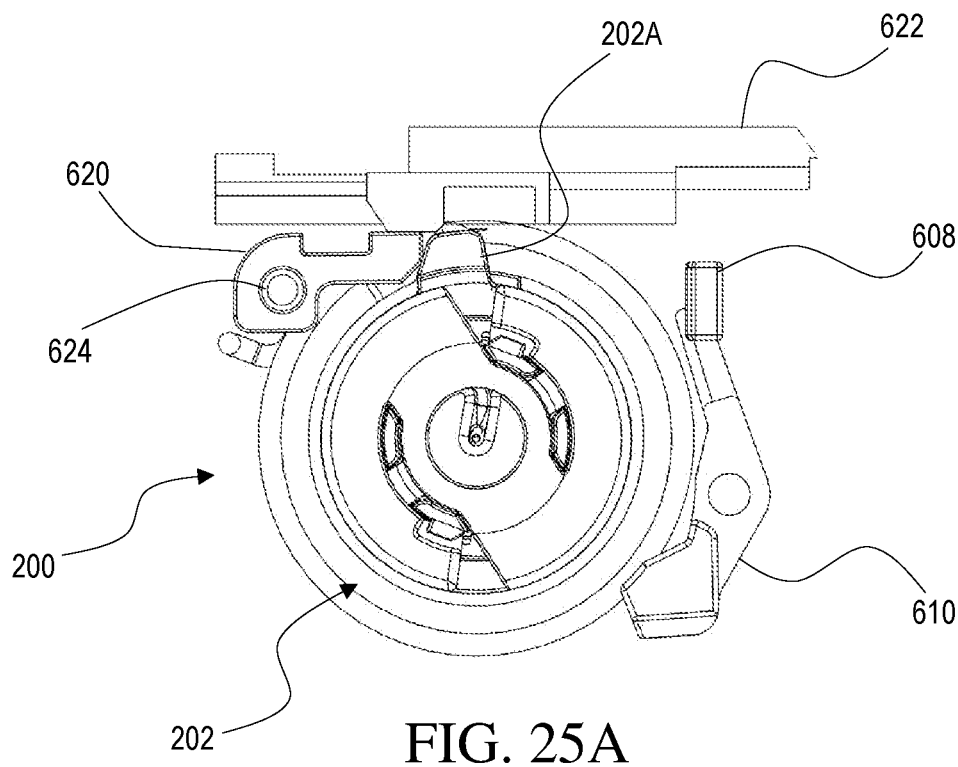
FIG. 25A is a top view of a NIM retraction mechanism according to at least one embodiment of the present invention in a delivery configuration.
Figure 25B:
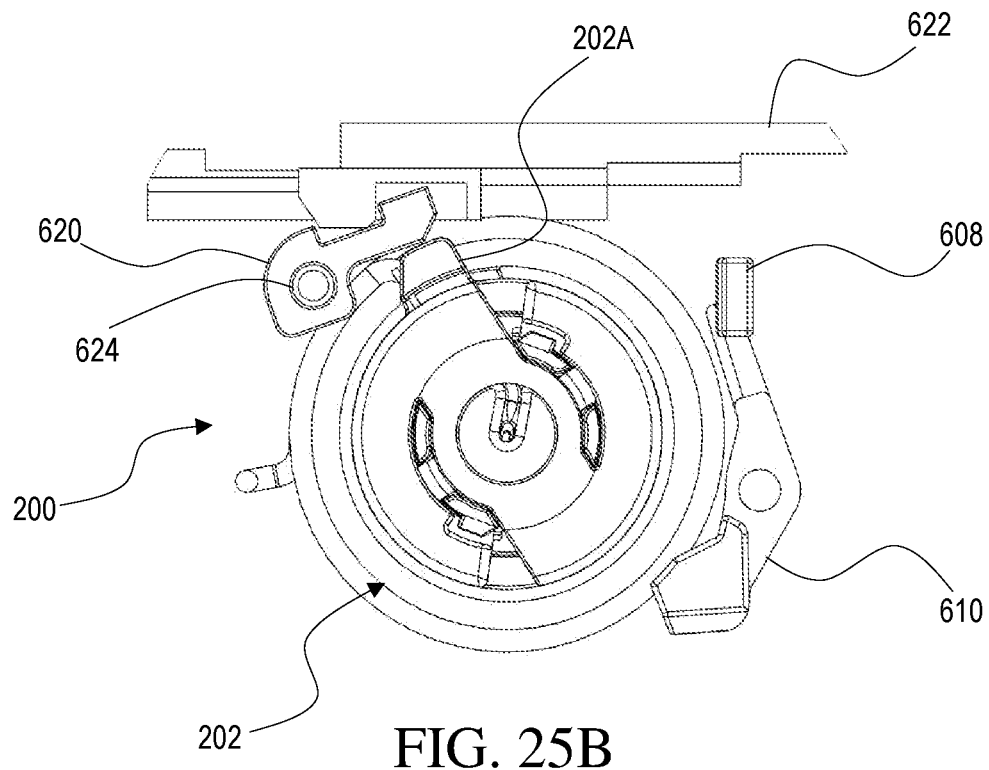
FIG. 25B is a top view of the NIM retraction mechanism of FIG. 25A in a retracted configuration.

As shown in FIGS. 25A-25B, the secondary or tertiary rotation of the housing may be controlled by a NIM retraction mechanism. In one example of a NIM retraction mechanism, with the needle and needle hub in the delivery position, protrusion 202A may be in contact with stop member 620, as shown in FIG. 25A. In this position, stop member 620 is prevented from rotating about spindle 624 by contact with slide member 622. Thus, further rotation of housing 202 is prevented. For example, in embodiments having a flexible cannula, such as that shown in FIGS. 14A-14C and described above, or as shown in FIGS. 17A-22 and described below, this position may correspond with the positions illustrated in FIG. 14C and FIG. 18C, respectively. In response to a triggering mechanism, slide member 622 may be displaced such that stop member 620 is able to rotate, about spindle 624, to the position shown in FIG. 25B. Hence, stop member 620 no longer restricts rotation of housing 202, allowing the needle to be fully retracted to a position in which medicament is no longer delivered to the target tissue, such as that shown in FIG. 16B and FIG. 17D. The triggering mechanism that causes displacement of slide member 622 may, for example, be caused by user input, a fault of the operation of the drug pump or any other event described above. In addition, displacement of slide member 622 may be purely mechanical or, alternatively, may be occur at least partially in response to a signal from power and control system 400.

Another embodiment is shown in FIGS. 17A-22. As in the embodiment of FIGS. 14A-14C described above, the present embodiment is configured to insert a flexible cannula into the target. For ease of understanding, structures in this embodiment are identified by the reference numbers utilized for similar structures in the first disclosed embodiment prefaced by the number "3", or as in the embodiment of FIGS. 14A-14C, changing the reference number from "2XXX" to "3XXX". That is structures are identified by "3XXX" wherein the "XXX" refers to similar structures in the first embodiment, or the similar structures in the embodiment of FIGS. 14A-14C identified by "2XXX". Accordingly, in the absence of a specific discussion below with regard to a reference number shown in FIGS. 17A-22, those of skill in the art will understand that structures identified by reference numbers "3XXX" refer to the same or similar structures as discussed with regard to the first or second embodiments.

The stages of operation are shown in three different cross-sections in FIGS. 17-19, while individual components clip 3286, cannula retainer 3282, needle hub 3212, and housing 3202 are illustrated in FIGS. 20-23, respectively. The first cross-section, shown in FIGS. 17A-17D, shows the interaction of followers 3212A of needle hub 3212 with guide surfaces 3204 of the housing 3202 at various stages of operation. Initially, as shown in FIG. 17A, hook arm 3212C is engaged with notch 3202C of housing 3202. This allows proper positioning and alignment of needle hub 3212 with respect to housing 3202.

Figure 17A:
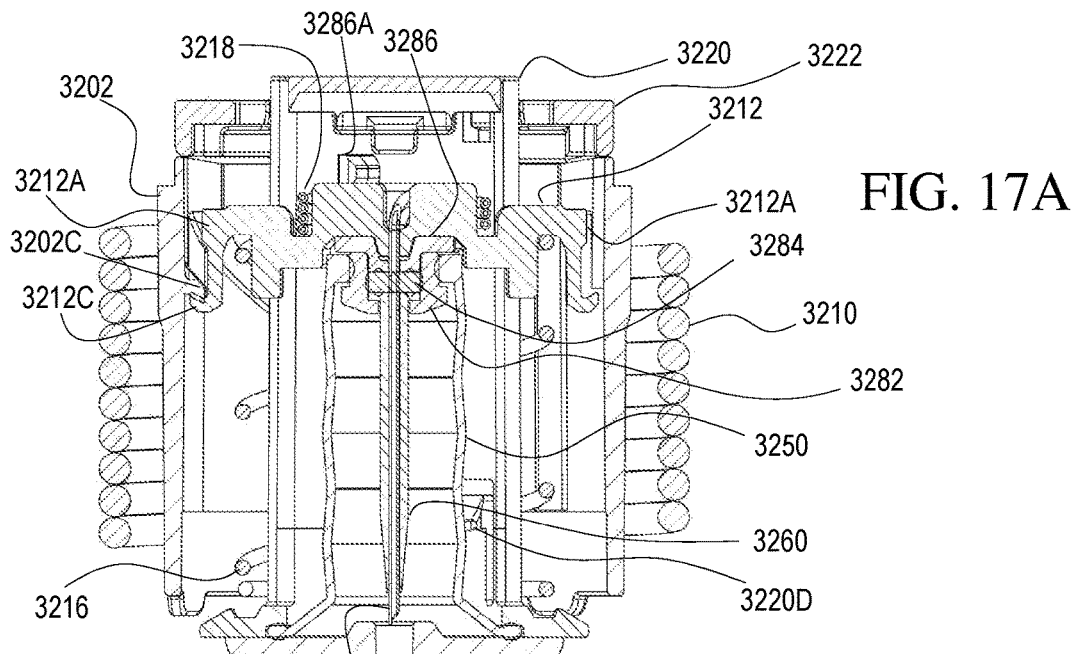
FIG. 17A shows a cross-sectional view of an insertion mechanism according to at least one embodiment of the present invention in an initial configuration.
Figure 17B:
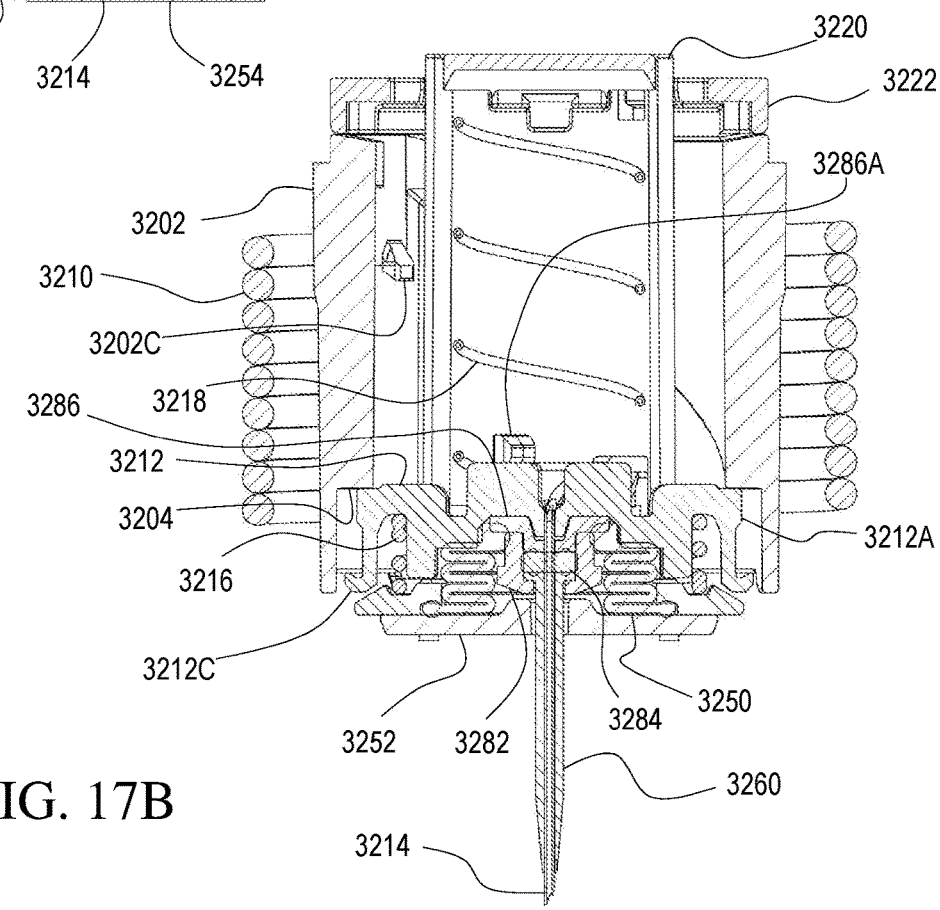
FIG. 17B shows a cross-sectional view of the insertion mechanism of FIG. 17A in an inserted configuration.

Rotation of the housing, caused by de-energizing of rotational biasing member 3210, disengages hook arm 3212C from notch 3202C. Further rotation of housing 3202, and contact between followers 3212A and guide surfaces 3204, causes needle hub 3212 to translate in the distal direction until needle 3214 and cannula 3260 are fully inserted in the target as shown in FIG. 17B.

Figure 17C:
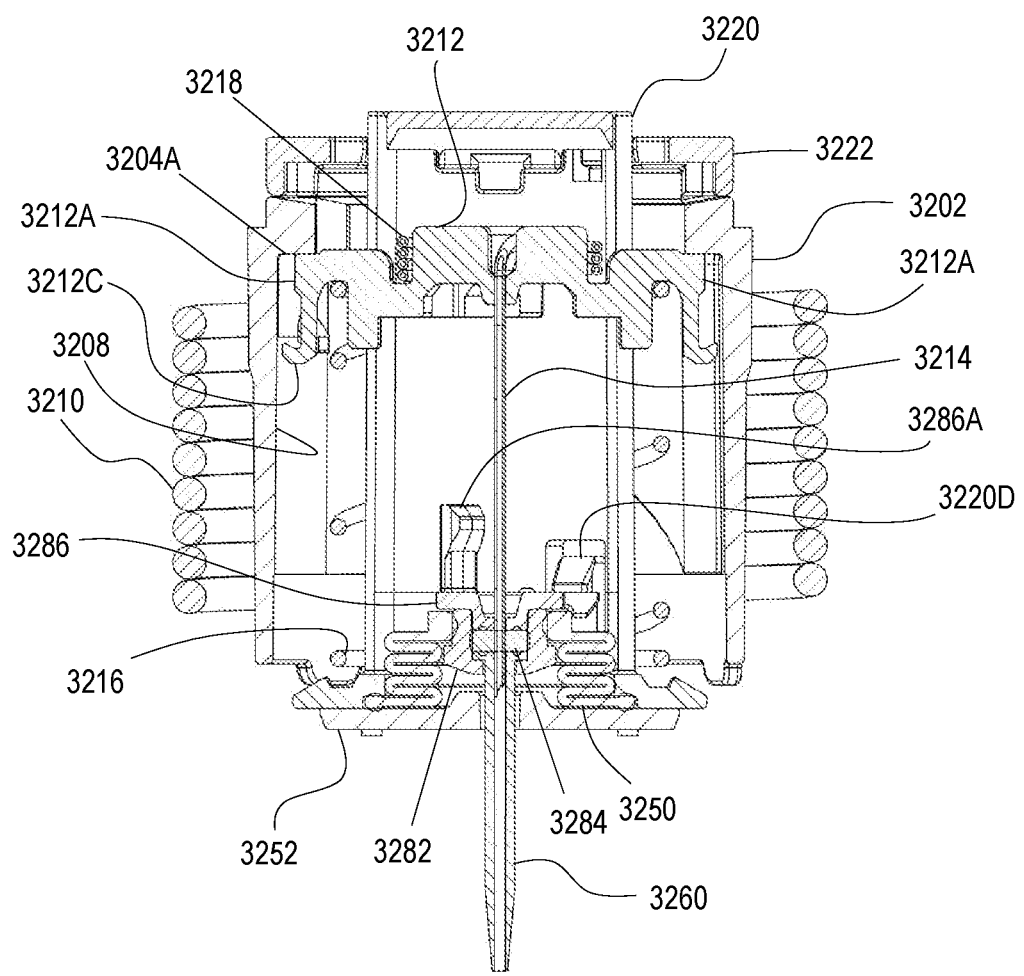
FIG. 17C shows a cross-sectional view of the insertion mechanism of FIG. 17A having the needle hub in a partially-retracted configuration.

After insertion of the needle 3214 and cannula 3260, continued, that is, secondary rotation of housing 3202 aligns axial slot 3208 of housing 3202 with followers 3212A. Hence, retraction biasing member 3216 is able to de-energize, which causes proximal translation of needle hub 3212 to the at least partially retracted position as shown in FIG. 17C. In this position, needle 3214 is at least partially disposed in cannula 3260 and through septum 3284 and followers 3212A are in contact with proximal portion 3204A of guide surfaces 3204. Therefore, contents may be delivered through needle 3214, cannula 3260, and to the target tissue.

Figure 17D:
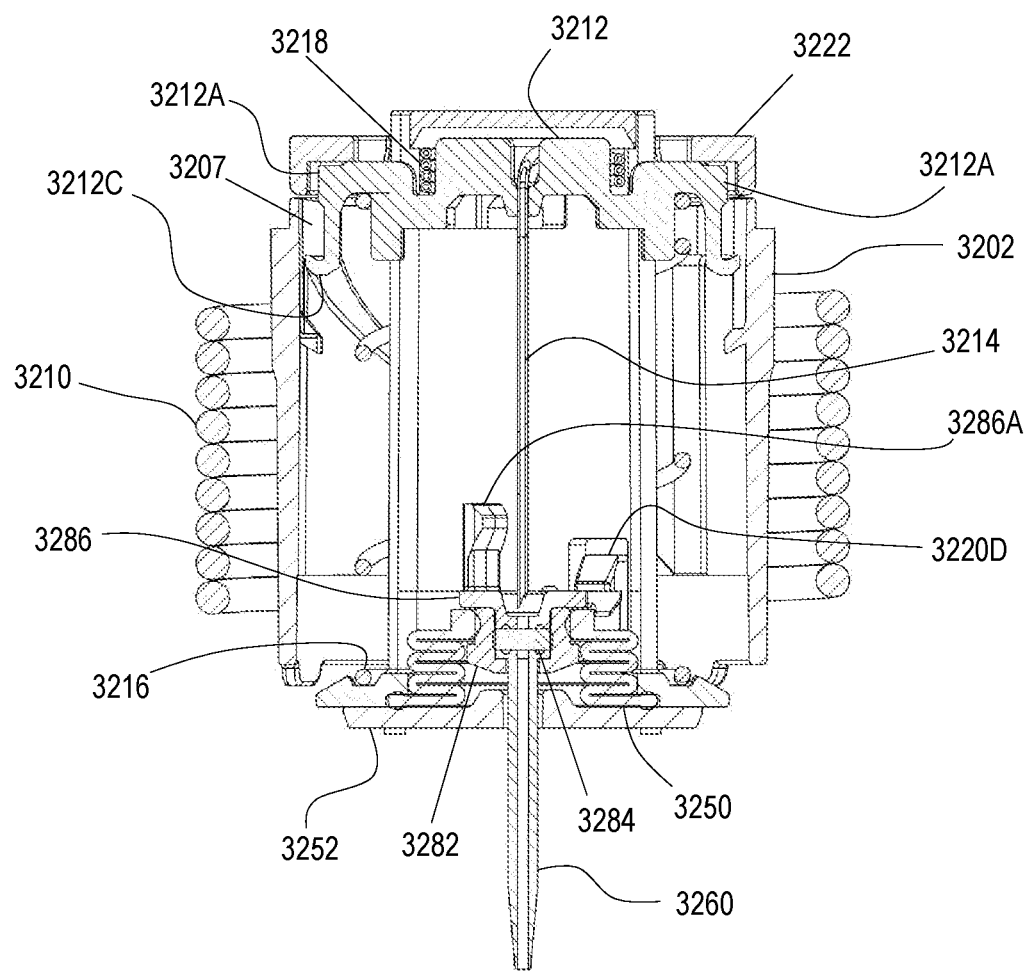
FIG. 17D shows a cross-sectional view of the insertion mechanism of FIG. 17A having the needle hub in a fully-retracted configuration.

In order to terminate delivery of medicament to the target tissue, continued rotation of housing 3202 may cause needle 3214 to be further retracted to the position shown in FIG. 17D. That is, as the housing 3200 is continued to rotate, for example, under the force of the rotation biasing member 3210, this tertiary rotation of the housing 3200 causes followers 3212A to disengage proximal portion 3204A and be aligned with retraction aperture 3207, thereby allowing additional proximal translation of needle hub 3212 in response to de-energizing of retraction biasing member 3216. In this position, needle 3214 is withdrawn from septum 3284. Hence, contents that flow through needle 3214 are not able to enter cannula 3260. Retraction of the needle may be caused by any of the safety mechanisms described, such as, for example, the safety mechanism illustrated in FIGS. 25A and 25B.

Figure 18A:
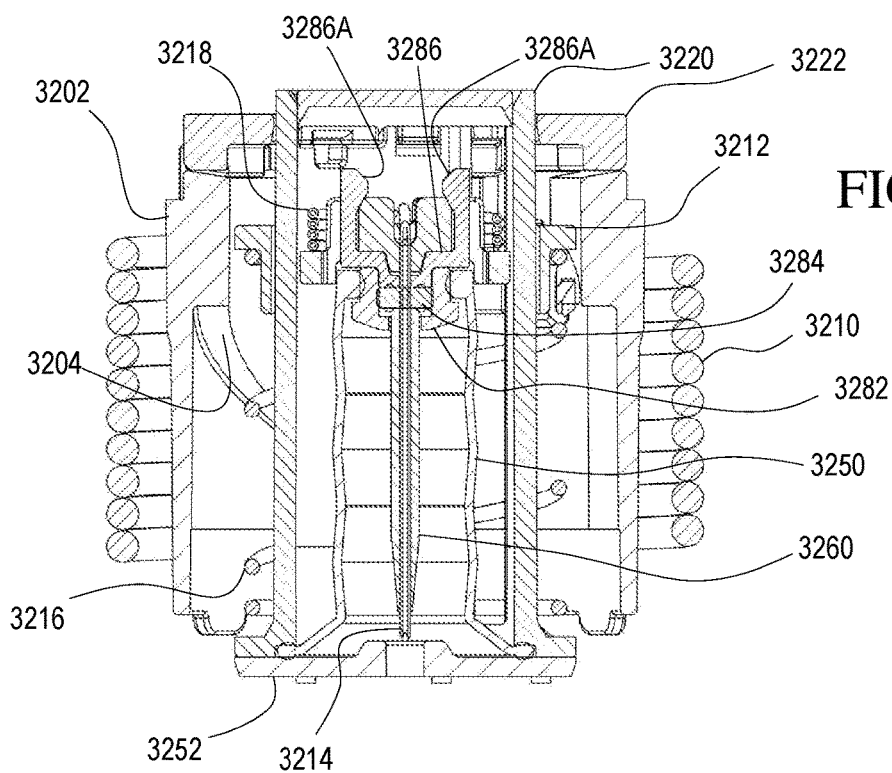
FIG. 18A shows a cross-sectional view of the insertion mechanism of FIG. 17A in an initial configuration taken at 45° rotation to the view of FIG. 17A.
Figure 18B:
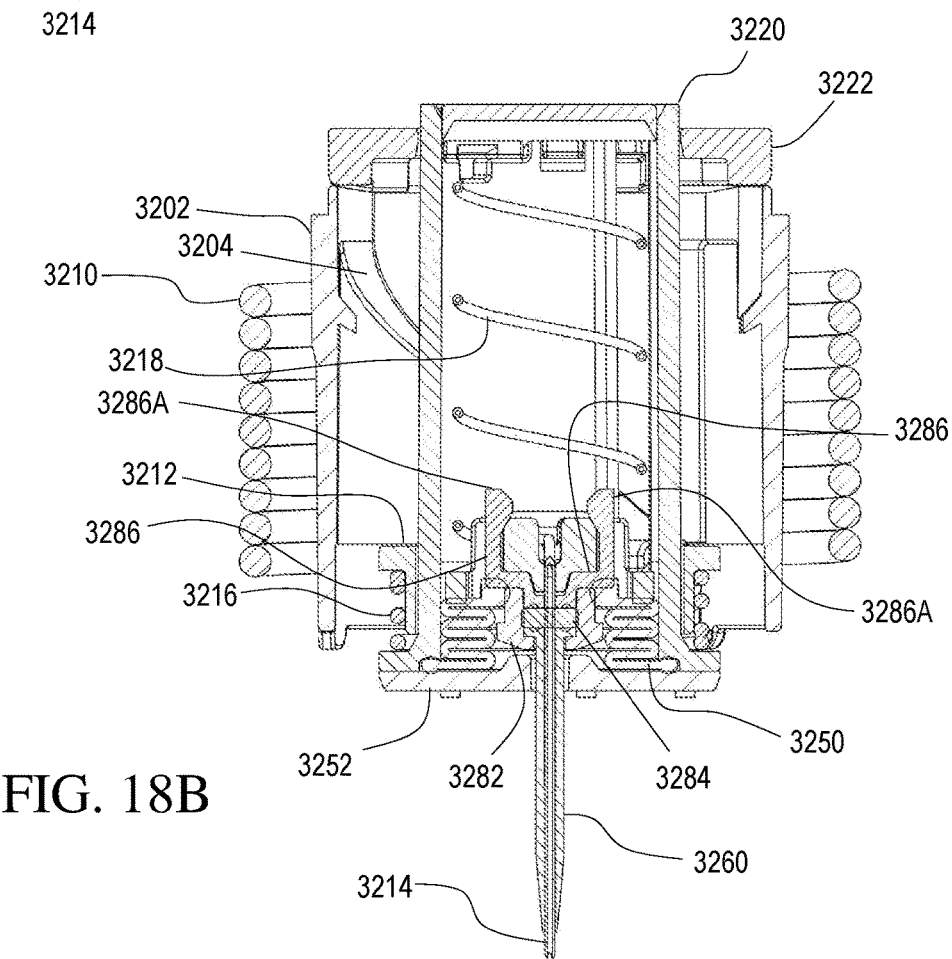
FIG. 18B shows a cross-sectional view of the insertion mechanism of FIG. 18A in an inserted configuration.
Figure 18C:
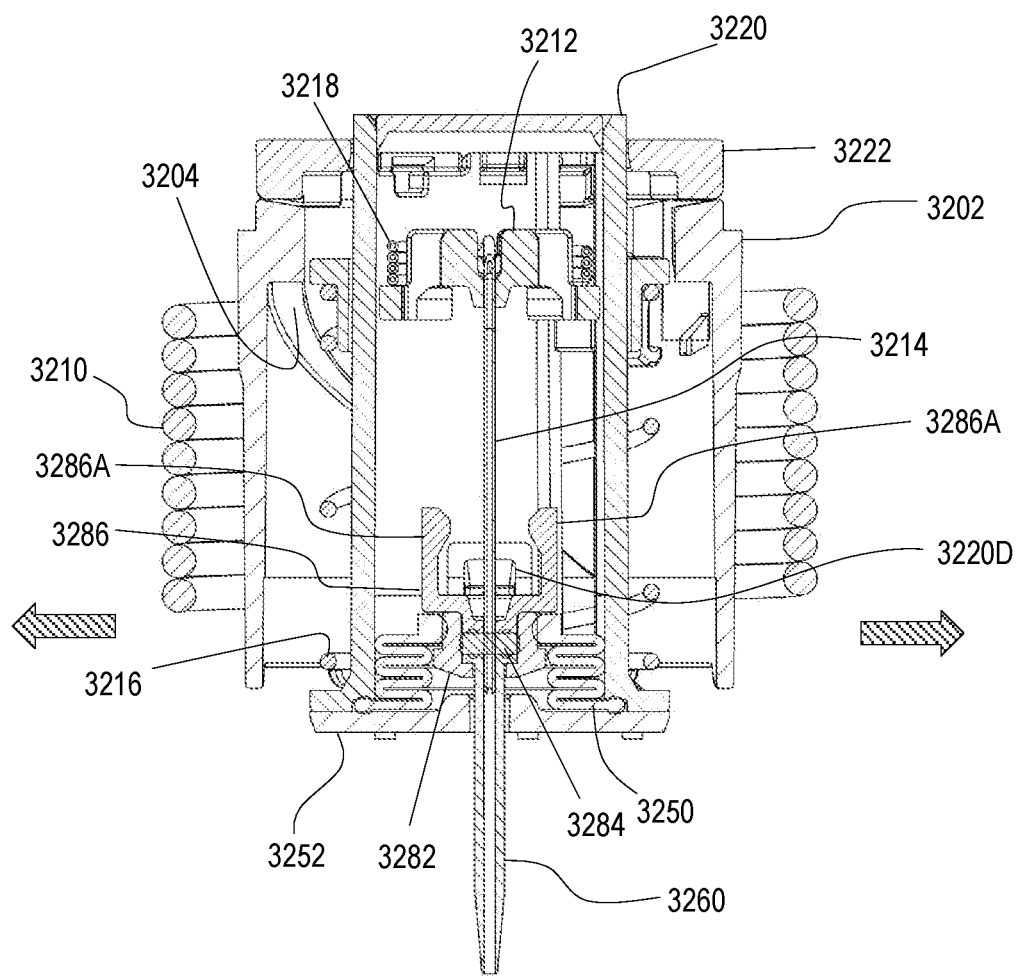
FIG. 18C shows a cross-sectional view of the insertion mechanism of FIG. 18A having the needle hub in a retracted configuration.
Figure 19A:
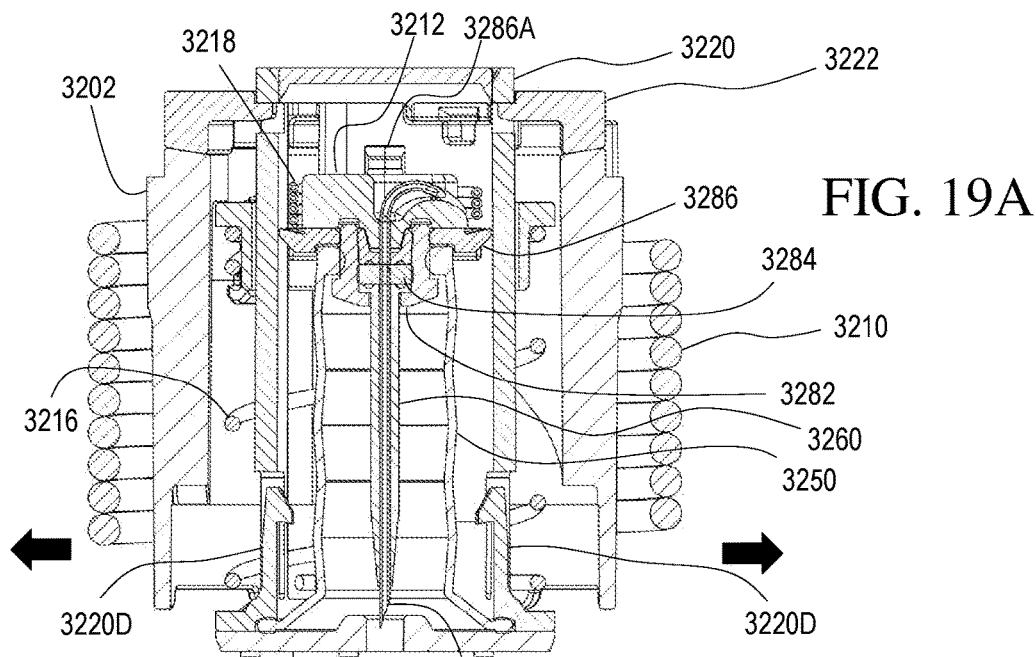
FIG. 19A shows a cross-sectional view of the insertion mechanism of FIGS. 17A and 18A in an initial configuration taken at 270° rotation to the view of FIG. 18A.
Figure 19B:
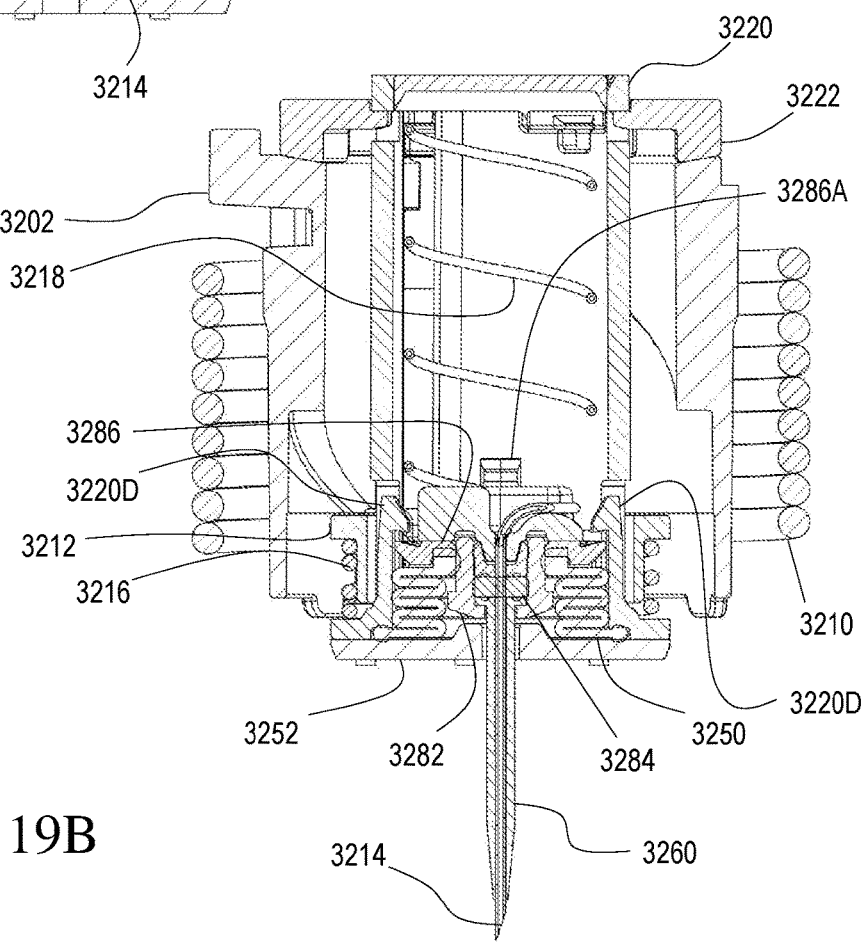
FIG. 19B shows a cross-sectional view of the insertion mechanism of FIG. 19A in an inserted configuration.
Figure 19C:
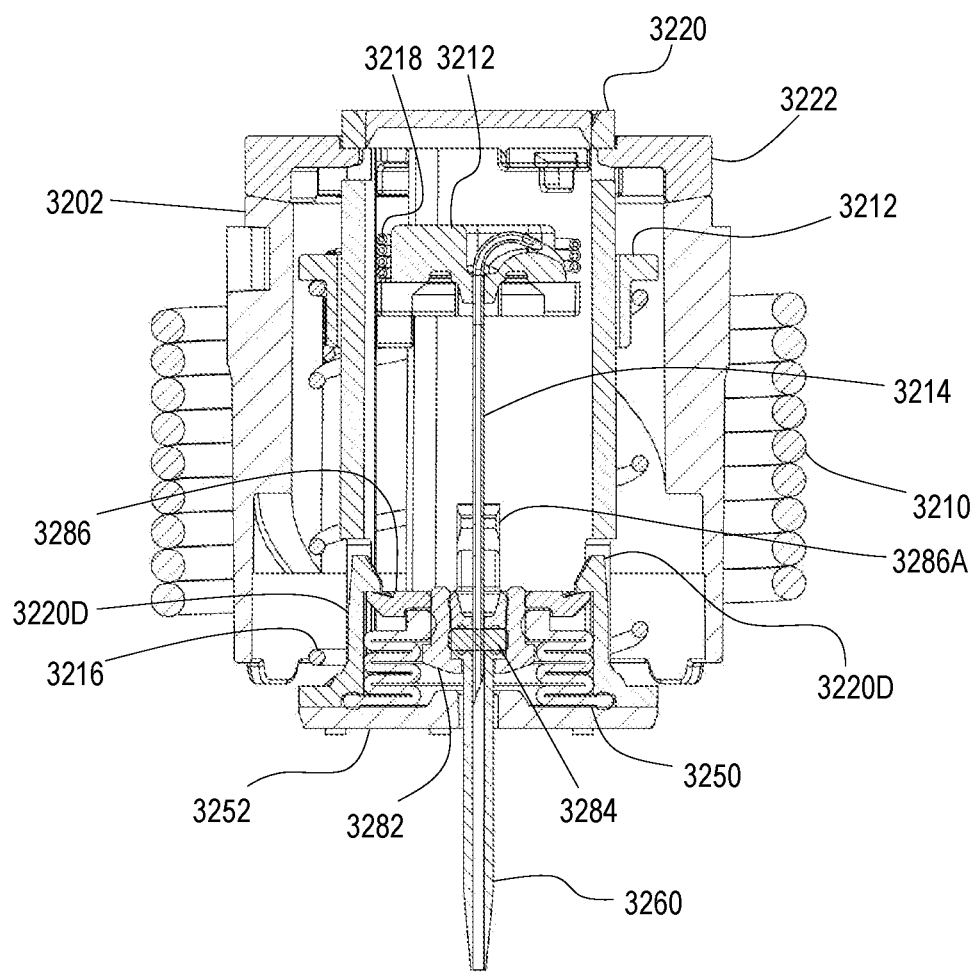
FIG. 19C shows a cross-sectional view of the insertion mechanism of FIG. 19A having the needle hub in a retracted configuration.

The second cross-section, shown in FIGS. 18A-18C, shows the interaction of connection arms 3286A of clip 3286 with needle hub 3212. The clip 3286 and the needle hub 3212 are shown in more detail in FIGS. 20 and 22, respectively. Initially, as seen in FIG. 18A, connection arms 3286A are engaged with needle hub 3212, thereby coupling axial translation of clip 3286 and needle hub 3212. As seen in FIG. 18B, connection arms 3286A remain engaged with needle hub 3212 as needle 3214 and cannula 3260 are inserted into the target. As will be described below, and as best seen in FIGS. 19A-19C, as clip 3286 translates in the distal direction it engages flex arms 3220D of sleeve 3220. Due to this engagement, clip 3286 is prevented from translating in the proximal direction. Hence, upon alignment of followers 3212A with proximal portion 3204A of guide surfaces 3204, connection arms 3286A disengage from needle hub 3212 by flexing outward (i.e., in the direction of the hatched arrows in FIG. 18C). As a result, upon alignment of followers 3212A with proximal portion 3204A of guide surfaces 3204, needle hub 3212 and needle 3214 translate in the proximal direction and needle 3214 is at least partially withdrawn from the target. Cannula 3260 remains disposed within the target.

Figure 20:
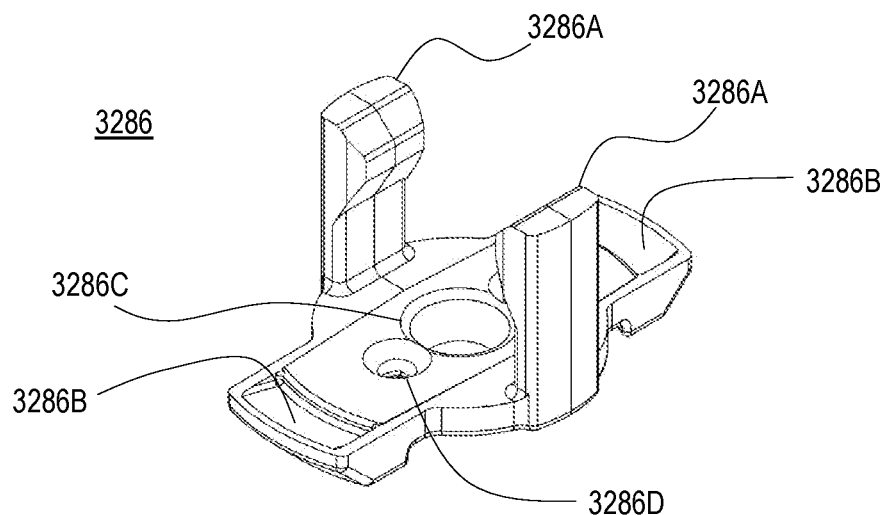
FIG. 20 is an isometric view of a clip illustrated in FIGS. 17A-19C.

The third cross-section is shown in FIGS. 19A-19C. The interaction between flex arms 3220D of sleeve 3220 and clip 3286 may be seen in these figures. As clip 3286 is translated distally during needle and cannula insertion, clip 3286 comes in contact with flex arms 3220D and causes them to be displaced outward (i.e., in the direction of the solid arrows shown in FIG. 19A). As shown in FIG. 19B, continued distal translation of clip 3286 allows flex-arms 3220D to at least partially return to their initial positions. As shown in FIG. 19C, as biasing member 3216 begins to expand, translation of clip 3286 is restricted by contact with flex arms 3220D. This restriction causes cannula 3260 to remain disposed within the target. As shown in FIG. 20, clip 3286 may include ramped surfaces 3286B configured to engage flex-arms 3320D. The ramped surfaces may create an undercut which ensures that contact of ramped surfaces 3286B with flex arms 3320D does not cause outward flexion of flex-arms 3320D.

Figure 21:
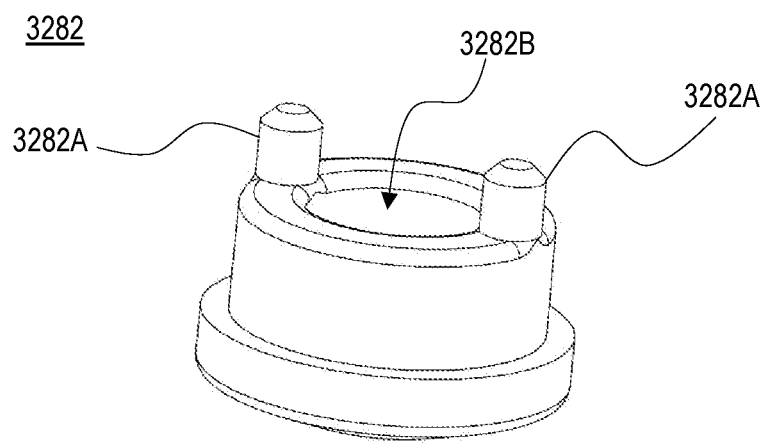
FIG. 21 is an isometric view of a cannula retainer illustrated in FIGS. 17A-19C.
Figure 22:
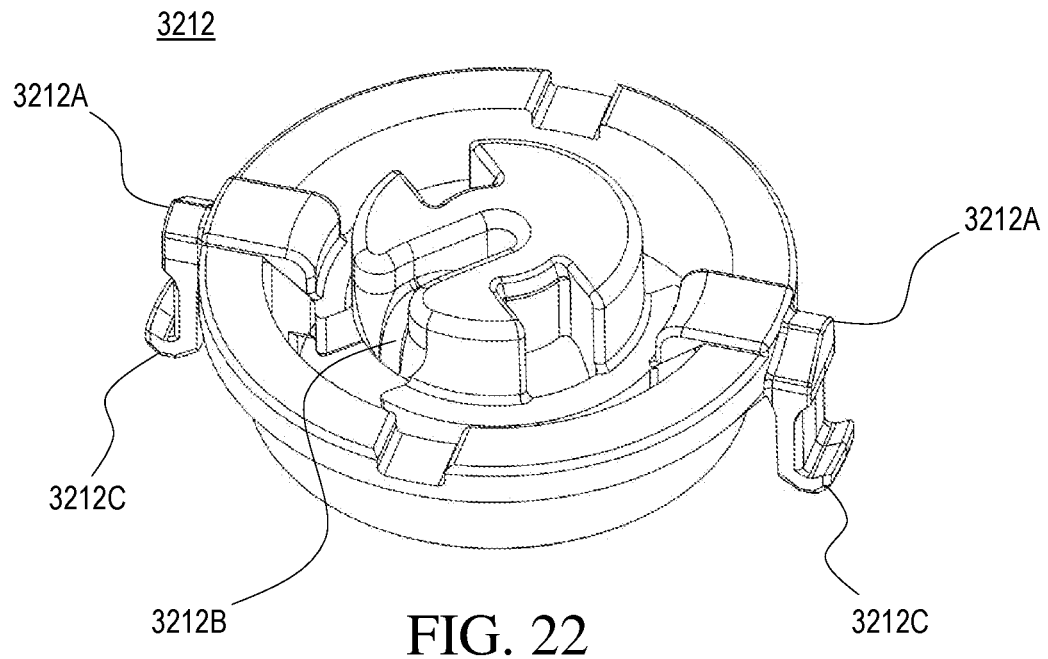
FIG. 22 is an isometric view of a needle hub illustrated in FIGS. 17A-19C.
Figure 23:
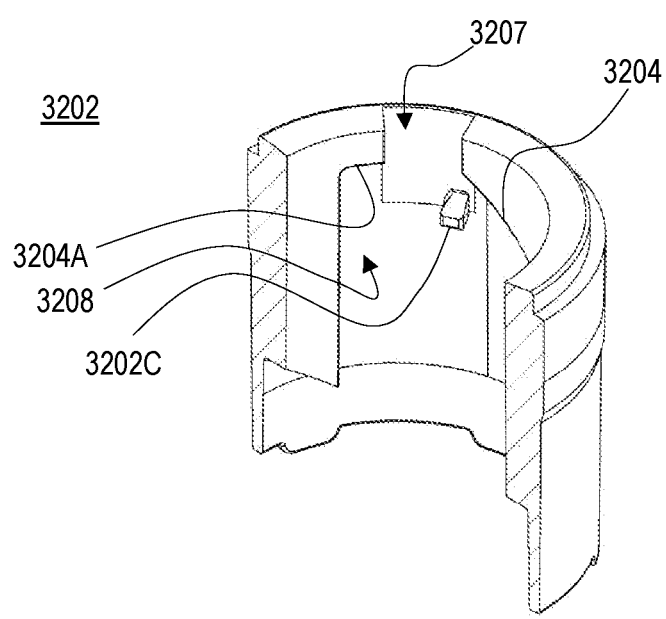
FIG. 23 is cross-sectional isometric view of a housing illustrated in FIGS. 17A-19C.

As shown in FIG. 21, cannula retainer 3282 includes bore 3282B and pins 3282A. As assembled, a shoulder of cannula 3260 and septum 3284 are disposed within bore 3282B. They are retained in this position by the position of clip 3286. Pins 3282A are configured to engage holes 3286D of clip 3286. This engagement may be configured to be a press-fit engagement to maintain the relative positions of cannula retainer 3282 and clip 3286. The central hole 3286C of the clip 3286 is adapted to receive needle 3214.

Certain optional standard components or variations of insertion mechanism 200 or drug pump 10 are contemplated while remaining within the breadth and scope of the present invention. For example, upper or lower housings may optionally contain one or more transparent or translucent windows 18, as shown in FIGS. 1A-1C, to enable the user to view the operation of the drug pump 10 or verify that drug dose has completed. Additionally, the drug pump 10 may contain an adhesive patch (not shown) and a patch liner (not shown) on the bottom surface of the housing 12. The adhesive patch may be utilized to adhere the drug pump 10 to the target tissue for delivery of the drug dose. As would be readily understood by one having ordinary skill in the art, the adhesive patch may have an adhesive surface for adhesion of the drug pump to the target tissue. The adhesive surface of the adhesive patch may initially be covered by a non-adhesive patch liner, which is removed from the adhesive patch prior to placement of the drug pump 10 in contact with the target tissue. Adhesive patch may optionally include a protective shroud that prevents actuation of the optional on-body sensor and covers base opening 252E. Removal of the patch liner may remove the protective shroud or the protective shroud may be removed separately. Removal of the patch liner may further remove the sealing membrane 254 of the insertion mechanism 200, opening the insertion mechanism to the target tissue for drug delivery.

Similarly, one or more of the components of insertion mechanism 200 and drug pump 10 may be modified while remaining functionally within the breadth and scope of the present invention. For example, as described above, while the housing of drug pump 10 is shown as two separate components, upper housing 12A and lower housing 12B, these components may be a single unified component. As discussed above, a glue, adhesive, or other known materials or methods may be utilized to affix one or more components of the insertion mechanism and/or drug pump to each other. Alternatively, one or more components of the insertion mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the insertion mechanisms and drug pumps disclosed herein provide an efficient and easily-operated system for automated drug delivery from a drug container. The novel embodiments described herein provide integrated safety features; enable direct user activation of the insertion mechanism; and are configured to maintain the sterility of the fluid pathway. As described above, the integrated safety features include optional on-body sensors, redundant lockouts, automated needle insertion and retraction upon user activation, and numerous user feedback options, including visual and auditory feedback options. The novel insertion mechanisms of the present invention may be directly activated by the user. For example, in at least one embodiment the rotation prevention feature, whether it is a stop component configured to engage protrusion 202A or a gear engaged with teeth of housing 202, which maintain the insertion mechanism in its locked, retracted state is directly displaced from its locked position by user depression of the activation mechanism. Alternatively, one or more additional components may be included, such as a spring mechanism, which displaces the rotation prevention feature upon direct displacement of the activation mechanism by the user without any intervening steps. In at least one configuration, rotation of a motor causes or allows rotation of a gear, thereby allowing rotation of the housing of the insertion mechanism.

Furthermore, the novel configurations of the insertion mechanism and drug pumps of the present invention maintain the sterility of the fluid pathway during storage, transportation, and through operation of the device. Because the path that the drug fluid travels within the device is entirely maintained in a sterile condition, only these components need to be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit of the present invention is that the components described herein are designed to be modular such that, for example, the housing and other components of the pump drug may readily be configured to accept and operate insertion mechanism 200 or a number of other variations of the insertion mechanism described herein.

Assembly and/or manufacturing of insertion mechanism 200, drug pump 10, or any of the individual components may utilize a number of known materials and methodologies in the art. For example, a number of known cleaning fluids such as isopropyl alcohol may be used to clean the components and/or the devices. A number of known adhesives or glues may similarly be employed in the manufacturing process. Additionally, known siliconization fluids and processes may be employed during the manufacture of the novel components and devices. Furthermore, known sterilization processes may be employed at one or more of the manufacturing or assembly stages to ensure the sterility of the final product.

In a further embodiment, the present invention provides a method of assembling the insertion mechanism including the steps of: connecting a hub to a proximal end of a needle; connecting a conduit to the hub; connecting a sterile boot to the hub; inserting a retraction biasing member into a sleeve of the needle insertion mechanism; inserting the hub, needle, conduit, and sterile boot into the sleeve (in this position, the retraction biasing member is constrained between the hub at one end and the sleeve at the other end); placing a housing around the sleeve; and connecting a base to the sleeve by engagement of flex arms with apertures in the housing. A rotational biasing member may be placed around the housing such that a portion of the rotational biasing member is engaged with a portion of the housing, thereby coupling de-energizing of the biasing member with rotation of the housing. Optionally, the method of assembly may further include the step of disposing a flexible cannula about the needle and within the sterile boot.

The distal end of the sterile boot may be positioned and held in fixed engagement with the distal end of the insertion mechanism housing by engagement of the housing with a base. In this position, the sterile boot is in an expanded configuration around the needle and/or cannula and creates an annular volume which may be sterile. A fluid conduit may be connected to the hub such that the fluid pathway, when open, travels directly from the fluid conduit, through the hub, and through the needle. A fluid pathway connection may be attached to the opposite end of the fluid conduit. The fluid pathway connection, and specifically a sterile sleeve of the fluid pathway connection, may be connected to a cap and pierceable seal of the drug container. The plunger seal and drive mechanism may be connected to the drug container at an end opposing the fluid pathway connection. A sealing membrane may be attached to the bottom of the base to close off the insertion mechanism from the environment. The components which constitute the pathway for fluid flow are now assembled. These components may be sterilized, by a number of known methods, and then mounted either fixedly or removably to an assembly platform or housing of the drug pump.

Manufacturing of a drug pump includes the step of attaching the base of the insertion mechanism to an assembly platform or housing of the drug pump. In at least one embodiment, the attachment is such that the base of the insertion mechanism is permitted to pass-through the assembly platform and/or housing to come in direct contact with the target tissue. The method of manufacturing further includes attachment of the fluid pathway connection, drug container, and drive mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the drug pump may include the steps of: activating, by a user, the activation mechanism; displacing a control arm to actuate an insertion mechanism; and actuating a power and control system to activate a drive control mechanism to drive fluid drug flow through the drug pump. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the body of a user.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A wearable drug delivery device comprising:
an outer housing;
a drug storage container positioned at least partially within the outer housing; and
an insertion mechanism positioned at least partially within the outer housing and including:
an insertion mechanism housing,
a rotational biasing member configured to rotate at least a portion of the insertion mechanism housing about an axis, wherein at least a portion of the rotational biasing member extends around the axis to form two or more revolutions around the axis and the at least a portion of the insertion mechanism housing,
a delivery member moveable between a first position wherein an insertion portion of the delivery member is positioned within the outer housing and a second position wherein the insertion portion of the delivery member is positioned exterior to the outer housing for insertion into a patient, and
a hub configured to:
(i) facilitate a connection between the delivery member and the drug storage container such that a fluid flow path passes through at least a portion of the hub during operation of the wearable drug delivery device, and
(ii) mechanically engage with the insertion mechanism housing such that initial rotation of the insertion mechanism housing with respect to the hub causes the delivery member to move along or parallel to the axis from the first position to the second position.

2. The wearable drug delivery device of claim 1, wherein the insertion mechanism housing comprises a cylindrical portion and at least a portion of the delivery member is positioned within the cylindrical portion when the delivery member is in the first position.

3. The wearable drug delivery device of claim 1, wherein the insertion mechanism housing comprises a first guide surface and the hub comprises an outwardly extending follower configured to slidably engage the first guide surface during rotation of the insertion mechanism housing.

4. The wearable drug delivery device of claim 3, wherein at least a portion of the first guide surface extends in an axial direction and a circumferential direction.

5. The wearable drug delivery device of claim 3, comprising a second guide surface fixed rotationally with respect to the outer housing, wherein the outwardly extending follower is configured to slidably engage the second guide surface to facilitate axial movement of the hub during rotation of the insertion mechanism housing.

6. The wearable drug delivery device of claim 1, wherein the insertion mechanism housing is rotatable about a rotational axis and the rotational axis is parallel to a longitudinal axis of the delivery member.

7. The wearable drug delivery device of claim 6, wherein the rotational axis of the insertion mechanism housing is coaxial with the longitudinal axis of the delivery member.

8. The wearable drug delivery device of claim 1, comprising a first abutment member having a first position wherein the first abutment member engages the insertion mechanism housing to prevent the rotational biasing member from rotating the insertion mechanism housing and a second position wherein the first abutment member is disengaged from the insertion mechanism housing to allow the rotational biasing member to rotate the insertion mechanism housing.

9. The wearable drug delivery device of claim 8, wherein the insertion mechanism housing includes a cylindrical portion and a second abutment member extending outwardly from the cylindrical portion, the second abutment member engaging the first abutment member when the first abutment member is in the first position.

10. The wearable drug delivery device of claim 1, comprising a drive mechanism positioned at least partially within the outer housing, the drive mechanism being configured to move a drug out of the drug storage container and into the patient via the delivery member.

11. The wearable drug delivery device of claim 1, comprising at least one fluid conduit defining at least a portion of the fluid flow path during operation of the wearable drug delivery device, the at least one fluid conduit being positioned at least partially in the outer housing and coupled with the hub to connect the delivery member in fluid communication with the drug storage container and such that at least a portion of the at least one fluid conduit and the hub translate jointly during insertion of the delivery member into the patient.

12. The wearable drug delivery device of claim 1, wherein the rotational biasing member comprises a torsion spring.

13. The wearable drug delivery device of claim 12, wherein at least a portion of the torsion spring directly contacts the insertion mechanism housing to apply a biasing force directly to the insertion mechanism housing.

14. The wearable drug delivery device of claim 1, wherein the delivery member comprises a needle.

15. The wearable drug delivery device of claim 14, wherein the needle has a hollow interior.

16. The wearable drug delivery device of claim 1, wherein at least a portion of the rotational biasing member surrounds the insertion mechanism housing.

17. The wearable drug delivery device of claim 16, wherein the insertion mechanism lacks a cover surrounding the rotational biasing member.

18. The wearable drug delivery device of claim 1, comprising an adhesive applied to a wall of the outer housing for attaching the outer housing to skin of the patient.

19. The wearable drug delivery device of claim 18, comprising an opening formed in the wall of the outer housing, wherein the insertion portion of the delivery member extends through the opening in the second position.

20. The wearable drug delivery device of claim 1, wherein the at least a portion of the rotational biasing member extends completely around at least a portion of the insertion mechanism housing.

21. The wearable drug delivery device of claim 1, wherein the at least a portion of the rotational biasing member comprises at least one coil wrapping around at least a portion of the insertion mechanism housing three or more times.

22. The wearable drug delivery device of claim 1, wherein the at least a portion of the rotational biasing member is centered around at least a portion of the delivery member.

23. The wearable drug delivery device of claim 1, comprising a radially outwardly extending protrusion configured to mechanically interact with the insertion mechanism housing such that the initial rotation of the insertion mechanism housing with respect to the hub causes the delivery member to move axially from the first position to the second position, wherein the radially outwardly extending protrusion is limited to one side of the hub.

24. The wearable drug delivery device of claim 1, comprising at least one fluid conduit directly connected to the hub and/or passing through at least a portion of the hub, wherein, during operation of the wearable drug delivery device, the at least one fluid conduit defines at least a portion of the fluid flow path and is not inserted into the patient.

25. The wearable drug delivery device of claim 1, wherein the rotational biasing member is configured to rotate the insertion mechanism housing in only a single rotational direction.

26. The wearable drug delivery device of claim 1, wherein the delivery member is fluidly coupled to the drug storage container via at least one fluid conduit at least prior to rotation of the insertion mechanism housing.

27. The wearable drug delivery device of claim 1, wherein the hub is configured to mechanically interact with the insertion mechanism housing by slidably engaging the insertion mechanism housing at least during rotation of the insertion mechanism housing.

28. A method comprising:
providing a wearable drug delivery device comprising an outer housing, a drug storage container positioned at least partially within the outer housing, and an insertion mechanism positioned at least partially within the outer housing, the insertion mechanism including an insertion mechanism housing, a rotational biasing member configured to rotate at least a portion of the insertion mechanism housing about an axis, at least a portion of the rotational biasing member extending around the axis to form two or more revolutions around the axis and the at least a portion of the insertion mechanism housing, a delivery member, a hub configured to (i) facilitate a connection between the delivery member and the drug storage container such that a fluid flow path passes through at least a portion of the hub during operation of the wearable drug delivery device, and (ii) mechanically engage with the insertion mechanism housing being such that initial rotation of the insertion mechanism housing with respect to the hub causes the delivery member to move in an axial direction;
positioning the outer housing in contact with a patient;
releasing the rotational biasing member to move the delivery member along or parallel to the axis from a first position wherein an insertion portion of the delivery member is positioned within the outer housing to a second position wherein the insertion portion of the delivery member is inserted into the patient; and
moving a drug out of the drug storage container into the patient via the delivery member.

29. The method of claim 28, wherein releasing the rotational biasing member comprises disengaging a first abutment member from a second abutment member extending outwardly from a cylindrical portion of the insertion mechanism housing.

30. The method of claim 28, wherein the delivery member is fluidly coupled to the drug storage container via at least one fluid conduit at least prior to rotation of the insertion mechanism housing.

31. The method of claim 28, wherein the hub is configured to mechanically interact with the insertion mechanism housing by slidably engaging the insertion mechanism housing at least during rotation of the insertion mechanism housing.

32. The method of claim 28, wherein the insertion mechanism housing comprises a first guide surface and the hub comprises an outwardly extending follower configured to slidably engage the first guide surface during rotation of the insertion mechanism housing.

33. The method of claim 28, wherein the wearable drug delivery device comprises at least one fluid conduit defining at least a portion of the fluid flow path during operation of the wearable drug delivery device, the at least one fluid conduit being positioned at least partially in the outer housing and coupled with the hub to connect the delivery member in fluid communication with the drug storage container and such that at least a portion of the at least one fluid conduit and the hub translate jointly during insertion of the delivery member into the patient.

34. The method of claim 28, wherein the wearable drug delivery device comprises a radially outwardly extending protrusion configured to mechanically interact with the insertion mechanism housing such that the initial rotation of the insertion mechanism housing with respect to the hub causes the delivery member to move axially from the first position to the second position, wherein the radially outwardly extending protrusion is limited to one side of the hub.

35. A wearable drug delivery device comprising:
 an outer housing;
 a drug storage container positioned at least partially within the outer housing; and
 an insertion mechanism positioned at least partially within the outer housing and including:
  an insertion mechanism housing,
  a rotational biasing member configured to rotate at least a portion of the insertion mechanism housing, wherein at least a portion of the rotational biasing member extends completely around the at least a portion of the insertion mechanism housing, and wherein the rotational biasing member is configured to rotate the insertion mechanism housing in only a single rotational direction,
  a delivery member moveable between a first position wherein an insertion portion of the delivery member is positioned within the outer housing and a second position wherein the insertion portion of the delivery member is positioned exterior to the outer housing for insertion into a patient, and
  a hub configured to:
   (i) facilitate a connection between the delivery member and the drug storage container such that a fluid flow path passes through at least a portion of the hub during operation of the wearable drug delivery device, and
   (ii) mechanically engage with the insertion mechanism housing such that initial rotation of the insertion mechanism housing with respect to the hub causes the delivery member to move axially from the first position to the second position.

36. The wearable drug delivery device of claim 35, wherein the delivery member is fluidly coupled to the drug storage container via at least one fluid conduit at least prior to rotation of the insertion mechanism housing.

37. The wearable drug delivery device of claim 35, wherein the hub is configured to mechanically interact with the insertion mechanism housing by slidably engaging the insertion mechanism housing at least during rotation of the insertion mechanism housing.

38. The wearable drug delivery device of claim 35, wherein the insertion mechanism housing comprises a first guide surface and the hub comprises an outwardly extending follower configured to slidably engage the first guide surface during rotation of the insertion mechanism housing.

39. The wearable drug delivery device of claim 35, comprising at least one fluid conduit defining at least a portion of the fluid flow path during operation of the wearable drug delivery device, the at least one fluid conduit being positioned at least partially in the outer housing and coupled with the hub to connect the delivery member in fluid communication with the drug storage container and such that at least a portion of the at least one fluid conduit and the hub translate jointly during insertion of the delivery member into the patient.

40. The wearable drug delivery device of claim 35, comprising a radially outwardly extending protrusion configured to mechanically interact with the insertion mechanism housing such that the initial rotation of the insertion mechanism housing with respect to the hub causes the delivery member to move axially from the first position to the second position, wherein the radially outwardly extending protrusion is limited to one side of the hub.

\* \* \* \* \*